(12) United States Patent
Spain et al.

(10) Patent No.: US 9,504,780 B2
(45) Date of Patent: Nov. 29, 2016

(54) EXTRACORPOREAL CLEARANCE OF ORGANOPHOSPHATES FROM BLOOD ON AN ACOUSTIC SEPARATION DEVICE

(71) Applicant: The Charles Stark Draper Laboratory, Inc., Cambridge, MA (US)

(72) Inventors: Tammy Spain, Oldsmar, FL (US); Jason O. Fiering, Boston, MA (US); Leila Albers, Tampa, FL (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 256 days.

(21) Appl. No.: 14/168,822

(22) Filed: Jan. 30, 2014

(65) Prior Publication Data
US 2014/0209542 A1    Jul. 31, 2014

Related U.S. Application Data

(60) Provisional application No. 61/758,495, filed on Jan. 30, 2013.

(51) Int. Cl.
*A61M 1/36*    (2006.01)

(52) U.S. Cl.
CPC ........... *A61M 1/362* (2014.02); *A61M 1/3678* (2014.02); *A61M 1/3693* (2013.01)

(58) Field of Classification Search
CPC . A61M 1/362; A61M 1/3678; A61M 1/3693
USPC .................. 210/251, 690; 435/197; 502/402
See application file for complete search history.

(56) References Cited

U.S. PATENT DOCUMENTS

| | | |
|---|---|---|
| 8,083,068 B2 | 12/2011 | Kaduchak et al. |
| 2004/0005582 A1 | 1/2004 | Shipwash |
| 2008/0181828 A1 | 7/2008 | Kluck |
| 2010/0006501 A1 | 1/2010 | Laurell et al. |
| 2010/0078384 A1 | 4/2010 | Yang |
| 2013/0043170 A1 | 2/2013 | Rose et al. |
| 2013/0048565 A1 | 2/2013 | Fiering et al. |

FOREIGN PATENT DOCUMENTS

| | | |
|---|---|---|
| EP | 0 914 184 A1 | 5/1999 |
| EP | 1 809 399 B1 | 8/2009 |
| EP | 2 145 687 A1 | 1/2010 |
| EP | 2 352 570 A2 | 8/2011 |
| WO | WO-02/12896 | 2/2002 |
| WO | WO-02/29400 | 4/2002 |
| WO | WO-2006/032703 | 3/2006 |

OTHER PUBLICATIONS

International Preliminary Report on Patentability issued Mar. 13, 2014 in PCT Application No. PCT/US2012/052886 (10 pages).
International Search Report and Written Opinion in PCT/US2014/022701 dated Jul. 18, 2014.
International Search Report and Written Opinion issued Dec. 11, 2012 in PCT Application No. PCT/US2012/052886.
US Non Final Office Action on U.S. Appl. No. 13/598,401 dated Jan. 2, 2015.
US Office Action in U.S. Appl. No. 13/598,401 DTD Jul. 1, 2015.
US Office Action in U.S. Appl. No. 13/598,401 DTD May 20, 2016.

*Primary Examiner* — Dirk Bass
(74) *Attorney, Agent, or Firm* — Christopher J. McKenna; Foley & Lardner LLP

(57) ABSTRACT

Systems, methods, and compositions for removing organophosphate toxins from blood are disclosed herein. The compositions include a lipid-based capture particle that displays BChE that binds to the toxin. The methods include acoustically separating toxins bound to lipid-based capture particles from blood factors of whole blood.

20 Claims, 8 Drawing Sheets

A)

B)

A)

B)

EXTRACORPOREAL CLEARANCE OF ORGANOPHOSPHATES FROM BLOOD ON AN ACOUSTIC SEPARATION DEVICE

CROSS-REFERENCE TO RELATED APPLICATIONS

This application claims priority to U.S. Application No. 61/758,495 filed Jan. 30, 2013. The entire contents of the application listed above are hereby incorporated by reference in their entirety.

BACKGROUND

Extracorporeal clearance of organophosphates (OP) from the blood is a technique to counter toxicity. Used as an adjuvant therapy, clearance of OP toxins makes other current therapeutic for clearance of OP toxins (for example, oximes or plasma administration) more effective. The most widely used method of extracorporeal OP clearance is hemodialysis, which is typically only effective with fat-insoluble toxins. Clearance of fat-soluble OP toxins, like parathion, or its active in vivo metabolite paraoxon, requires hemoperfusion over adsorbent surfaces like activated charcoal or activated resins. The resins used to remove fat-soluble toxins, e.g., paraoxon, can also non-specifically adsorb or damage blood factors (e.g., platelets, red blood cells, white blood cells, etc.), which can lead to clinical complications such as loss of platelets, leukopenia, hypocalcaemia, hypoglycemia, and fibrinogen reduction. The loss of blood factors can lead to systemic bleeding, which can cause death in patients receiving this treatment.

SUMMARY

In one aspect, the present technology provides devices for removing organophosphates from whole blood including: a thermoplastic microfluidic separation channel having an upstream end and downstream end, wherein the separation channel comprises: 1) a first inlet configured to introduce flowing whole blood into a proximal end of the separation channel, wherein the whole blood comprises plasma, blood factors, and organophosphates; 2) a first outlet at the downstream end of the separation channel positioned substantially along the longitudinal axis of the separation channel; and 3) a second outlet at the downstream end positioned adjacent a first wall of the separation channel; and the device includes an acoustic transducer positioned adjacent to the separation channel for imposing a standing acoustic wave transverse to the flow of blood through a particle migration region of the separation channel; and a lipid-based capture particle injector containing lipid-based capture particles and configured to introduce lipid-based capture particles into the whole blood before the blood reaches the particle migration region of the separation channel, wherein the lipid-based capture particle comprises a first population of lipids, and silicon oil; wherein the first population of lipids comprises organophosphate affinity molecules linked to the lipids of first population of lipids. In some implementations, lipid-based particle also includes a second population of lipids, wherein the second population of lipids form a lipid layer in which the first population is embedded.

In some implementations, the lipid-based capture particles are in the form of a liposome, vesicle, emulsion, lipid encapsulated droplet, or combinations thereof. In some implementations, the lipid-based capture particle is a liposome.

In some implementations, the organophosphate affinity molecule is BChE.

In some implementations, the organophosphate affinity molecules are linked to the first population of lipids via PEG.

In some implementations, the silicone oil is encapsulated within the lipid-based particle.

In some implementations, the device also includes a reservoir in fluidic communication with the lipid-based capture particle injector.

In some implementations, the separation channel comprises walls having a thickness at a particle aggregation point that is a multiple of one quarter of the wavelength of an acoustic wave acting on the walls of the separation channel.

In another aspect, the present technology provides methods of cleansing blood of a subject including: flowing whole blood into an inlet of a microfluidic separation channel wherein the whole blood comprises plasma, blood factors, and organophosphates; introducing lipid-based capture particles into the whole blood which bind to the organophosphates, wherein the lipid-based capture particle comprises a first population of lipids, a second population of lipids, silicon oil and cholesterol; wherein the first population of lipids comprises an organophosphate affinity molecule linked to the lipids of the first population of lipids; and applying a standing acoustic wave transverse to a direction of flow of the whole blood through the separation channel such that the blood factors aggregate to about the axial center of the separation channel and the lipid-based capture particles with bound organophosphates aggregate along at least one wall of the separation channel. In some implementations, the methods also include cycling off the standing acoustic wave such that the duty cycle of the standing acoustic wave is between about 75% and about 95%.

In some implementations, the methods also include collecting blood factors of the whole blood at a first outlet positioned at a downstream end of the separation channel at about the axial center of the separation channel.

In some implementations, the methods also include collecting lipid-based capture particles through at least a second outlet positioned at the downstream end of the separation channel adjacent to the at least one wall along which the lipid-based capture particles are aggregated.

In some implementations, the lipid-based capture particle also include a second population of lipids, wherein the second population of lipids form a lipid layer in which the first population is embedded. In some implementations, the lipid-based capture particles have an opposite contrast factor than the blood factors.

In some implementations, the lipid-based capture particles are between about 10 µm and 20 µm in diameter.

In some implementations, the methods also include reintroducing the blood factors back into the subject after flowing the whole blood through the microfluidic separation channel.

In another aspect, the present technology provides compositions including organophosphate affinity molecules, a first population of lipids and silicon oil, wherein the first population of lipids comprises organophosphates affinity molecules linked to the lipids of the first population of lipid, wherein the silicone oil is encapsulated within the lipid-based capture particle, and the at least one organophosphate affinity molecule is displayed on the surface of the lipid-based capture particle.

In some implementations, the organophosphate affinity molecule is BChE.

In some implementations, the first population of lipids is selected from DSPE, DPPE, DMPE, or a combination thereof.

In some implementations, the lipid-based capture particle also includes a second population of lipids, wherein the second population of lipids form a lipid layer in which the first population is embedded. In some implementations, the second population of lipids is selected from DOPC, DOPG, DOPE, or a combination thereof.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

Figure 1:
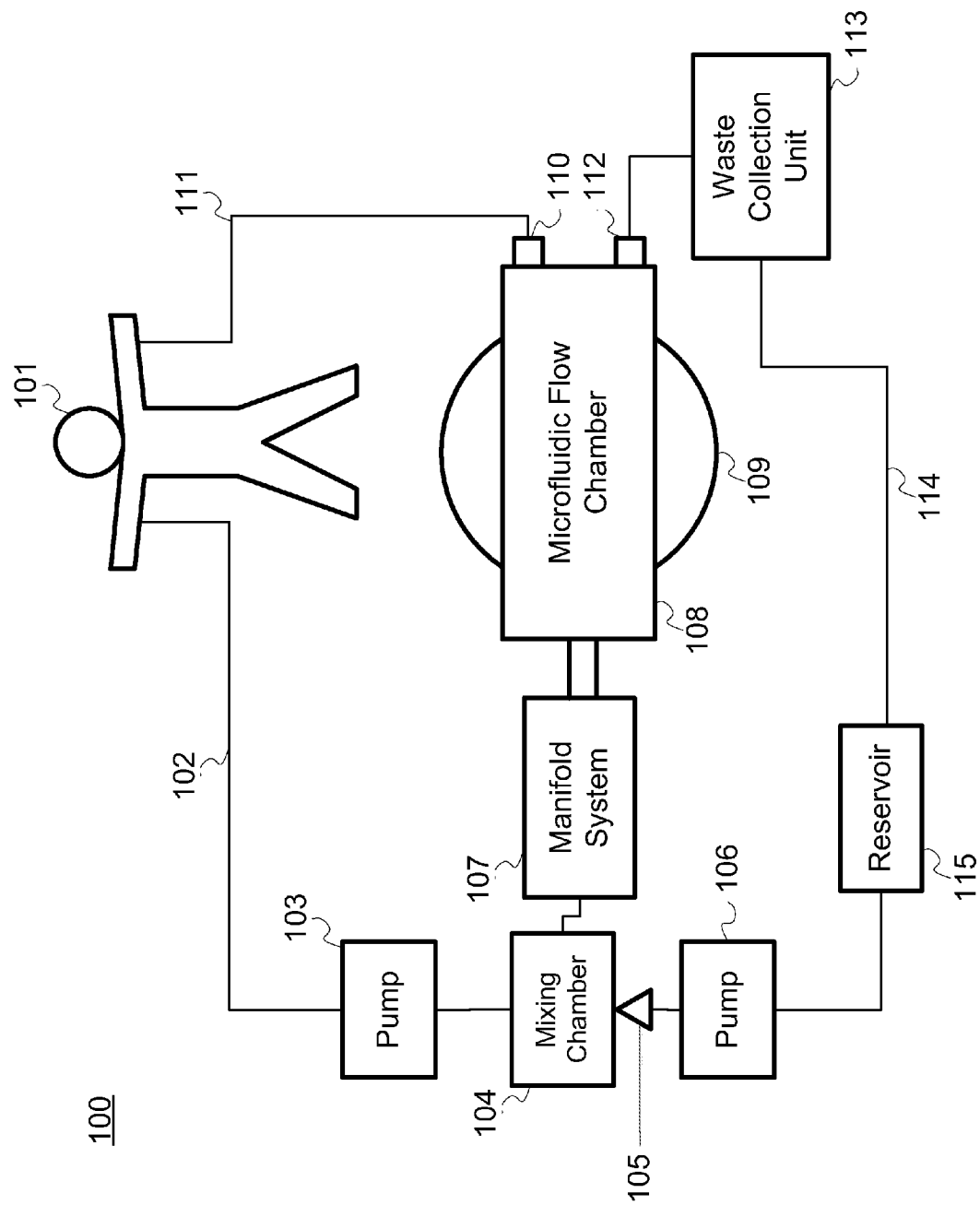
FIG. 1 is a non-limiting, exemplary block diagram of a system for removing organophosphates from a patient.

The various concepts introduced above and discussed in greater detail below may be implemented in any of numerous ways, as the described concepts are not limited to any particular manner of implementation. Examples of specific implementations and applications are provided primarily for illustrative purposes.

As used in this specification and the appended claims, the singular forms "a", "an" and "the" include plural referents unless the content clearly dictates otherwise. For example, reference to "a cell" includes a combination of two or more cells, and the like.

As used herein, "organophosphate affinity molecule" ("OP affinity molecule") refers to a molecule that binds to organophosphates. By way of example, but not by limitation, butyrylcholinesterase (BChE) is an organophosphate affinity molecule that binds to parathion and/or paraoxon, which are organophosphates.

As used herein, "blood factors" refers to elements in the blood required for the normal function of blood. Whole blood includes, but is not limited to, plasma and blood factors. Blood factors include, but are not limited to, platelets, red blood cells, and white blood cells. By way of example, but not by limitations, loss of normal blood function can be caused by a loss of, for example, platelets, leukopenia, hypocalcaemia, hypoglycemia, and fibrinogen reduction.

As used herein, "lipid-based capture particle(s)" refers to a composition including a first population of lipids, silicone oil, and at least one organophosphate affinity molecule which is displayed on the surface of the lipid-based capture particle. In some implementations, the lipid-based capture particles include cholesterol. In some implementations, the first population of lipids is linked to at least one organophosphate affinity molecule via a PEG linker. In some implementations, the lipid-based capture particle further comprises a second population of lipids, wherein the second population of lipids provide a lipid layer in which the first population of lipids is embedded. Examples of organophosphate affinity molecules include, but are not limited to, butyrylcholinesterase (BChE). In some implementations, the lipid-based capture particles are in the form of liposomes, vesicles, emulsions, lipid encapsulated droplets or combinations thereof.

Generally, the present technology relates to compositions, systems, devices, and methods for removing organophosphates (OP), e.g., parathion and/or paraoxon, from whole blood. Parathion is a fat-soluble OP pesticide. Paraoxon is the active metabolite of parathion.

In various implementations, the disclosure relates to removing OP, e.g., parathion and/or paraoxon, from whole blood by acoustically separating OP from the blood via high throughput microfluidic arrays. In some implementations, lipid-based capture particles displaying at least one organophosphate affinity molecule are introduced and mixed with the blood, ex vivo, to form complexes with the OP, yielding complexes that are effectively and efficiently separated from the blood factors and plasma by acoustic separation. The lipid-based capture particles typically bind to the OP.

The lipid-based capture particles can be administered to whole blood of animals, e.g., humans, that have been exposed to OP, e.g., parathion, or suspected of being exposed to OP to facilitate the removal of OP from the blood.

Lipid-Based Capture Particles

In some implementations, the lipid-based capture particles of the present technology are in the form of liposomes vesicles, emulsions, lipid encapsulated droplets or combinations thereof. In some implementations, a lipid-based capture particle is in the form of a liposome. In some implementations, the liposome includes a first population of lipids and a second population of lipids, wherein the second population of lipids provide a lipid layer in which the first population of lipids is embedded. In some implementations, the first population of lipids is linked to at least one organophosphate affinity molecule. Examples of organophosphate affinity molecule include, but are not limited to, butyrylcholinesterase (BChE) molecule. BChE is a non-specific cholinesterase enzyme that hydrolyses many different choline esters. BChE can bind to parathion and/or paraoxon. In some implementations, the first population of lipids is linked to BChE.

In some implementations, the organophosphate affinity molecule, e.g., BChE, is linked to the lipid (e.g., the first population of lipids) via a PEG linker to form an organophosphate affinity molecule-PEG-lipid complex, e.g., BChE-PEG-lipid. In some implementations, a first population of lipids is linked to a plurality of PEG molecules to form one or more PEG-lipids. In some implementations, the PEG-lipid is linked to BChE. In some implementations, the PEG is linked to the BChE, and the PEG-BChE is linked to the lipid. In some implementation the lipids comprising the first population of lipids includes, but is not limited to, synthetic, semi-synthetic, or naturally occurring lipids. By way of example, but not by way of limitation, in some implementations, the lipids comprising the first population of lipids is one or more of 1,2-Distearoyl-sn-glycero-3-phosphoethanolamine (DSPE), N-(Carbonyl-methoxypolyethyleneglycol 2000)-1,2-dipalmitoyl-sn-glycero-3-phosphoethanolamine (DPPE), and N-(Carbonyl-methoxypolyethyleneglycol 2000)-1,2-dimyristoyl-sn-glycero-3-phosphoethanolamine (DMPE).

In some implementations, at least one organophosphate affinity molecule-PEG-lipid complex, e.g., BChE-PEG-lipid, is combined with a second population of lipids to form a lipid-based capture particle, e.g., a liposome. In some implementations, the second population of lipids provide a lipid layer, e.g., a lipid-bilayer, in which the first population of lipids is embedded. In some implementations, the second population of lipids are the same lipid. In some implementations, the second population of lipids comprises a mixture of different lipids. In some implementations, the lipids of the first population and the second population are the same. In some implementations, the lipids of the first population and the second population are different. In some implementations, the second population of lipids includes but is not limited to one or more of synthetic, semi-synthetic, or naturally occurring lipids. By way of example, but not by way of limitation, the second population of lipids includes one or more of 1,2-dioleoyl-sn-glycero-3-phosphocholine (DOPC), 1,2-dioleoyl-sn-glycero-3-phospho-(1'-rac-glycerol) (DOPG) and 1,2-dioleoyl-sn-glycero-3-phosphoethanolamine (DOPE).

In some implementations, the lipid-based capture particle also includes silicone oil. In some implementations, the silicone oil is encapsulated within the lipid-based capture particle. In some implementations, the viscosity of the silicone oil is about 100, about 200, about 300, about 400, about 500, about 600, about 700, about 800, about 900, about 1000 centistokes, or ranges between any two of these values. In another implementation, the viscosity of the silicone oil is between about 1000 to 10,000, or between about 2000 to 9000, or between about 3000 to 8000, or between about 4000 to 7000, or between about 5000 to 6000 centistokes.

Additionally or alternatively, in some implementation, the liposome of the lipid-based capture particle includes cholesterol. In some implementations, the lipid mixture includes between about 0.01 to 1 mol %, between about 1 to 5 mol %, between about 5 to 40 mol %, between about 10 to 35 mol %, between about 15 to 30 mol %, or between about 20 to about 25 mol % of cholesterol.

Additionally or alternatively, in some implementation, the liposome of the lipid-based capture particle also includes one or more active molecules. An active molecule is incorporated into the liposome for its effect on the liposome density and acoustic activity. Example of active molecule includes, but is not limited to, per-fluoro-butane and ultrasound imaging contrast agents.

Methods for Making the Lipid-based Capture Particles

Methods for Linking Organophosphate Affinity Molecule to a Lipid

In some implementation, organophosphate affinity molecule, e.g., BChE, is linked to PEG. In some implementations, BChE is presented as a mixture containing monomers, dimers, and tetramers of BChE. In some implementations, PEG is mixed with the BChE mixture at about an 80:1 ratio, which produces 1:1 ratio of PEG to BChE monomeric unit with high percentage of dimers being produced.

In some implementations, PEG is linked to N-Hydroxy succinimide (NHS). In some implementations, the NHS-PEG is linked to the organophosphate affinity molecule. In some implementations, the NHS-PEG is linked to BChE. In some implementation, the PEG in NHS-PEG links to lysine residues or the N-terminus of BChE. In some implementations, a NHS-activated PEG is linked to a phospholipid, i.e., NHS-PEG-DSPE. In some implementations, the NHS-PEG-DSPE is linked to BChE, i.e., BChE-PEG-phospholipid.

In another implementation, N-terminal thiol groups are targeted by activated PEG-o-pyridylthioester. In some implementations, N-terminal thiol groups targeting is performed after the PEG-o-pyridylthioester is linked to a lipid. In some implementations, cysteine-functionalized phospholipids are linked to PEG, e.g., Cys-PEG-DSPE, In yet another implementation, PEG functionalized phospholipids are linked to sialic acid sugars. Sialic acid sugar facilitates conjugation of glycans on BChE. In some implementations, the PEG functionalized phospholipid is linked to at least one BChE. PEG functionalized phospholipids include, but are not limited to, DSPE-PEG-NH$_2$ and DSPE-PEG-COOH.

In some implementations, conjugation of BChE to PEG-phospholipids includes the dissolution of an activated PEG functionalized lipid, e.g., DSPE-PEG-NH$_2$, in an organic solvent such as 1:2 ratio of DMSO/methanol, the addition of BChE and coupling reagent EDC. In some implementations, the reaction can be monitored by thin layer chromatography (TLC) using KMnO$_4$ or p-anisaldehyde. In some implementations, the un-reacted lipid-PEG can be extracted by gel electrophoresis.

In some implementations, about 10 to 50-fold molar excess of functionalized PEG-lipid, e.g., NHS-PEG-DSPE, is combined with organophosphate affinity molecules to produce organophosphate affinity molecules-PEG-lipid complexes, e.g., BChE-PEG-DSPE. In some implementations, the organophosphate affinity molecules e.g., BChE, are first dissolved in a conjugation buffer (e.g., sodium bicarbonate 100 mM buffer, pH 8.5 or other amine-free buffer at pH 7-8.5). In some implementations, the functionalized PEG-lipid are added next at a final concentration of at least 10 mg/ml. Additionally, or alternatively, in some implementations, the functionalized PEG-lipid are added next at a final concentration of 10 to 50-fold molar excess. In some implementations, the mixture is mixed for about 30 to 60 minutes at room temperature. In another implementation, the mixture is mixed for about 2 hours at 4° C.

In some implementations, the further purification of BChE-PEG-phospholipid is performed by size exclusion chromatography (SEC). SEC can be performed using Sepharose or Superdex™ 200, which is not only useful for purification of the protein product but also maps the location of the PEG-bound sites within the protein by trypsin digestion.

In some implementations, the purity of the BChE-PEG-phospholipid is determined. Purity can be determined by commonly used methods in the art including, but not limited to, SDS-PAGE, mass spectroscopy, and HPLC.

In some implementations, the location or the site of the PEG attachment to the BChE is identified by peptide mapping followed by LC/MS or LC/MS/MS analysis.

Method for Making Affinity Molecule Displaying Lipid-Based Capture Particles

In some implementations, the conjugated BChE-PEG-lipids, described above, are incorporated into a lipid-based capture particle.

In some implementations, at least one BChE-PEG-lipid is combined with a mixture of lipids, e.g., a second population of lipids, to form a lipid-based capture particle. In some implementations, the second population of lipids provide a lipid layer, e.g., a lipid-bilayer, in which the first population of lipids is embedded. In some implementation, the mixture of lipids, e.g., a second population of lipids, includes cholesterol. In some implementations, silicone oil with different viscosity is employed in different formulations to further enhance the flow efficiency of the lipid-based capture particles through the device. In some implementations, active molecules, such as per-fluoro-butane, are incorporated for their effect on the lipid-based particle's density and acoustic activity.

In some implementations, the mixture of lipids, e.g., a second population of lipids, includes, but is not limited to, synthetic, semi-synthetic, or naturally occurring lipids. In some implementations, the mixture of lipids is selected from 1,2-dioleoyl-sn-glycero-3-phosphocholine (DOPC), 1,2-dioleoyl-sn-glycero-3-phospho-(1'-rac-glycerol) (DOPG) and 1,2-dioleoyl-sn-glycero-3-phosphoethanolamine (DOPE).

In some implementations, the lipid-based capture particle also includes silicone oil. In some implementations, the silicone oil is encapsulated within the lipid-based capture particle. In some implementations, the viscosity of the silicone oil is about 100, about 200, about 300, about 400, about 500, about 600, about 700, about 800, about 900, about 1000 centistokes, or ranges between any two of these values. In another implementation, the viscosity of the silicone oil is between about 1000 to 10,000, or between about 2000 to 9000, or between about 3000 to 8000, or between about 4000 to 7000, or between about 5000 to 6000 centistokes.

Additionally or alternatively, in some implementation, the lipid-based capture particle also includes cholesterol. In some implementations, the lipid mixture includes between about 5 to 40 mol %, or between about 10 to 35 mol %, or between about 15 to 30 mol %, or between about 20 to about 25 mol % of cholesterol.

In some implementations, the lipid-based particle comprises between about 1 to 30 mol % of BChE-PEG-lipids, between about 5 to 40 mol % of cholesterol, between about 5 to 20 mol % of silicone oil, and between about 50 to 85 mol % of the mixture of lipids.

In some implementations, the size and monodispersity of the lipid-based capture particles are controlled by modified extrusion techniques, and dialysis/diafiltration. In some implementations, film rehydration technique to provide large vesicles with diameter of 15-30 μm. In some implementations, hydration of the lipid film in warm (35° C.) water followed by addition of re-hydrated buffer to pre-hydrated lipid film. In some implementations, the re-hydrated lipid-buffer solution is incubated for several hours at a temperature above lipid phase transition temperature, e.g., >10° C. In some implementations, the lipid-based capture particles swell and strip away from a Teflon surface producing small cloud of lipid-based capture particles that can be harvested by a Pasteur Pipette.

The formation of liposomes, vesicles, emulsions, and lipid encapsulated droplets is known in the art, and the compositions and methods disclosed herein are not intended to be limited by the method of formation of these structures. By way of example, but not by way of limitation, known methods may be used to form the lipid-based particles disclosed herein; additionally or alternatively, the methods described herein may also be used.

In some implementations, dynamic light scattering (DLS) and transmission electron microscopy (TEM) is used to determine the final size and dispersion of the lipid-based capture particles. In some implementations, lipid ratio in the lipid-based capture particles is determined by analysis such as, but limited to, HPLC, GPC, and/or MALDI-MS. In some implementations, the extent of BChE-PEG-lipid conjugation is monitored by incorporation of fluorescent dye (e.g., Calcein) in the lipid-based capture particle and measuring the amount of BChE before and after Calcein leakage by spectrophotometer.

In some implementations, BChE enzyme activity in lipid-based capture particles is assayed by a modified Ellman activity assay to ensure BChE retained its enzymatic activity. The assay detects the activity of BChE by measuring the formation of a substrate hydrolysis product that absorbs at 412 nm.

In some implementations, the ability of the lipid-based capture particle to clear organophosphates, e.g., parathion and/or paraoxon, from blood is determined in vitro. In some implementations, up to five different concentrations of the lipid-based capture particle is added to blood that has been contaminated with excess paraoxon. In some implementations, the blood is incubated at 37° C. for one hour and filtered using a commercially available filter plate (molecular weight cutoff ultrafiltration) to remove parathion and/or paraoxon that is bound to the BChE in the blood. In some implementations, the concentration of unbound parathion and/or paraoxon in the blood filtrate is determined by GC-MS.

In some implementations, after incubation at 37° C. for one hour, the lipid-based capture particles bound with organophosphates, e.g., parathion and/or paraoxon, is separated from the blood via an acoustic device and system as described below. In some implementations, the blood is pumped into at least one channel of a microfluidic devices. In some implementations, the blood is subjected to an acoustic wave in the channel. In some implementations, the acoustic wave separates the lipid-based capture particles bound with organophosphates, e.g., parathion and/or paraoxon, from the blood factors and the lipid-based capture particles bound with parathion and/or paraoxon selectively removed.

Devices and Systems FIG. 1 illustrates a system 100 for removing organophosphates, e.g., parathion and/or paraoxon, from the blood. In the system 100, organophosphate contaminated blood is removed from a patient via an intravenous line 102. The blood is then pumped to a mixing chamber 104 by a first pump 103. In the mixing chamber 104, lipid-based capture particles are mixed with whole blood. In some implementations, the components of the lipid-based capture particles are stored in a reservoir 115. In some implementations, the lipid-based capture particles are formed and are stored in the reservoir 115. From the reservoir 115, the lipid-based capture particles are pumped by a second pump 106 into the mixing chamber. In some implementations, the lipid-based capture particles are formed as the contents of the reservoir 115 are extruded from a micronozzle 105 at the entrance to the mixing chamber 104. In the mixing chamber 1-4, the affinity molecules on the lipid-based capture particles, e.g., BChE, bind to the organophosphates, e.g., parathion and/or paraoxon. From the mixing chamber 104, the whole blood and lipid-based capture particles enter a manifold system 107. The manifold system 107 distributes the whole blood and lipid-based capture particles to a plurality of separation channels contained within the microfluidic flow chamber 108. The microfluidic flow chamber 108 is in contact with or in functional proximity, e.g., sits atop, at least one bulk piezoelectric acoustic transducer 109. The acoustic waves generated by the bulk piezoelectric acoustic transducers are used to funnel the contents of the whole blood and lipid-based capture particles with bound organophosphates to specific outlets of the separation channels. As the whole blood flows through the microfluidic flow chamber 108, cleansed blood flows to a first outlet 110. After exiting the first outlet 100, the cleansed blood returns to the patient 101, via a second intravenous line 111. The lipid-based capture particles and other waste material removed from the blood exit the microfluidic flow chamber 108 via a second outlet 112. Next, the waste material and lipid-based capture particles enter a waste collection unit 113. In the waste collection unit 113, the lipid-based capture particles are separated from the waste material. Once separated, the waste material is discarded and the lipid-based capture particles are returned to the reservoir 107 by tubing 114. Once returned to the reservoir 107, the lipid-based capture particles are reused in the system to remove additional waste material from whole blood as it continues to flow through the system.

The system 100, as illustrated, includes a pump 103 for moving blood from the patient 101 to the mixing chamber 104. In some implementations, the pump operates continuously, while in other implementations the pump works intermittently, and only activates when the level of whole blood in the mixing chamber 104 or manifold falls below a set threshold. In some implementations, the flow rate of the pump is configurable, such that the rate the blood exits the patient can be configured to be faster or slower than if no pump was used. In yet other implementations, no external pump is required. In this example, the blood is transported to the mixing chamber 104 by the pressure generated by the patient's own heart. In some implementations, the patient 101 is connected to a blood pressure monitor, which in turn controls the pump. Example pumps can include, but are not limited, to peristaltic pumps or any other pump suitable for flowing blood.

As illustrated in the system 100, lipid-based capture particles are also pumped into the mixing chamber. A second pump 106 pumps the ingredients to form the lipid-based capture particles from a reservoir 107 to the mixing chamber 104. In some implementations, the components of the lipid-based capture particles are continuously agitated in the reservoir 107 in order to keep the components well mixed. The components are formed into lipid-based capture particles as they enter the mixing chamber 104. The components enter the mixing chamber 104 through a micronozzle 105. In some implementations, the lipid-based capture particles are formed in the reservoir 107. In some implementations, the micronozzle 105 injects the lipid-based capture particles into the mixing chamber 104. In other implementations, the micronozzle 105 injects the lipid-based capture particles into the manifold system 107, and in yet other implementations the micronozzle 105 is positioned such that it injects lipid-based capture particles directly into the separation channels of the microfluidic chamber 108. In some implementations, the micronozzle 105 is a micro-machined nozzle, configured to allow a specific amount of the lipid-based capture particle components through the nozzle at a given time. In some implementations, the micronozzle is an array of micronozzles. In yet other implementations, the micronozzle is a membrane with pores. In some implementations, the pump 106 is configured to flow the contents of the reservoir through the micronozzle 105 at a predetermined rate such that the amphipathic characteristics of the molecules of the components of the captures particles cause the lipid-based capture particles to spontaneously form as they exit the micronozzle 105.

In some implementations, a micronozzle is not used to generate the lipid-based capture particles. In these implementations, the lipid-based capture particles are premade. The lipid-based capture particles are then stored in the reservoir and then introduced into the system by the pump 106 at either the mixing chamber 104, manifold system 107, and/or the separation channels of the microfluidic flow chamber 108.

As illustrated in system 100, the whole blood containing organophosphates, e.g., parathion and/or paraoxon, and the lipid-based capture particles enter the mixing chamber 104. In some implantations, the contents of the mixing chamber are continuously agitated to improve distribution of the lipid-based capture particles throughout the whole blood and organophosphates such that the lipid-based capture particles bind to the organophosphates. In some implementations, anticoagulants or blood thinners are introduced into the mixing chamber 104 to assist the blood as it flows through the system 100. In some implementations, the mixing chamber 104 contains a heating element for warming the contents of the mixing chamber 104.

The contents of the mixing chamber 104 then flow into the manifold system 107, as illustrated by system 100. The manifold system 107 flows the whole blood, organophosphates, e.g., parathion and/or paraoxon, and lipid-based capture particles into the inlets of the plurality of separation channels of the microfluidic flow chamber 108.

In the illustrated system 100, the microfluidic flow chamber 108 contains a plurality of separation channels. The lipid-based capture particles and organophosphates, are driven with standing acoustic waves to outlets. In some implementations, the separation occurs during a single stage, while in other implementations, the separation occurs over a plurality of stages. In some implementations, the microfluidic flow chamber is disposable.

As show in the illustrations of system 100, the microfluidic flow chamber 108 sits atop a bulk piezoelectric acoustic transducer 109. In some implementations, the system 100 contains a single bulk piezoelectric acoustic transducer 109, while in other implementations the system 100 contains a plurality of bulk piezoelectric acoustic transducers 109.

In some implementations, the bulk piezoelectric acoustic transducer 109 is glued to the microfluidic flow chamber 108. In other implementations the microfluidic flow chamber 108 is clamped to the bulk piezoelectric acoustic transducer 109 so the microfluidic flow chamber may easily be removed from the system. In other implementations the adhesive material connecting the bulk piezoelectric acoustic transducer 109 to the microfluidic flow chamber 108 is removable, for example by heating the adhesive.

The bulk piezoelectric acoustic transducer 109 imposes a standing acoustic wave on the separation channels of the microfluidic flow chamber 108 transverse to the flow of the fluid within the microfluidic flow chamber 108. The standing acoustic waves are used to drive fluid constituents towards or away from the walls of the separation channels or other aggregation axes.

Figure 5:
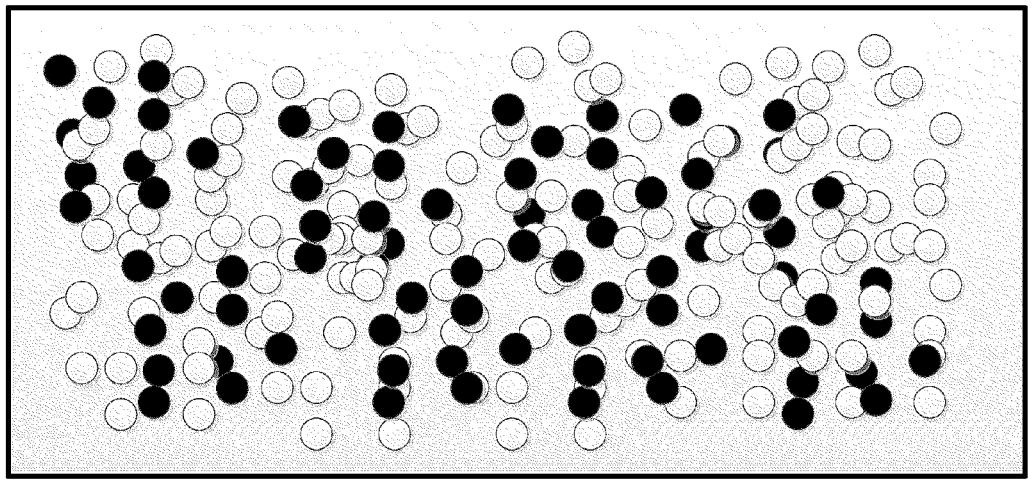
FIG. 5A is a non-limiting, exemplary cross sectional view a single-stage separation channel, as depicted in FIG. 2, containing a plurality of particles lacking an active acoustic transducer.
FIG. 5B is a non-limiting, exemplary cross sectional of a single-stage separation channel, as depicted in FIG. 2, containing a plurality of particles adjacent to an active acoustic transducer.
Figure 5:
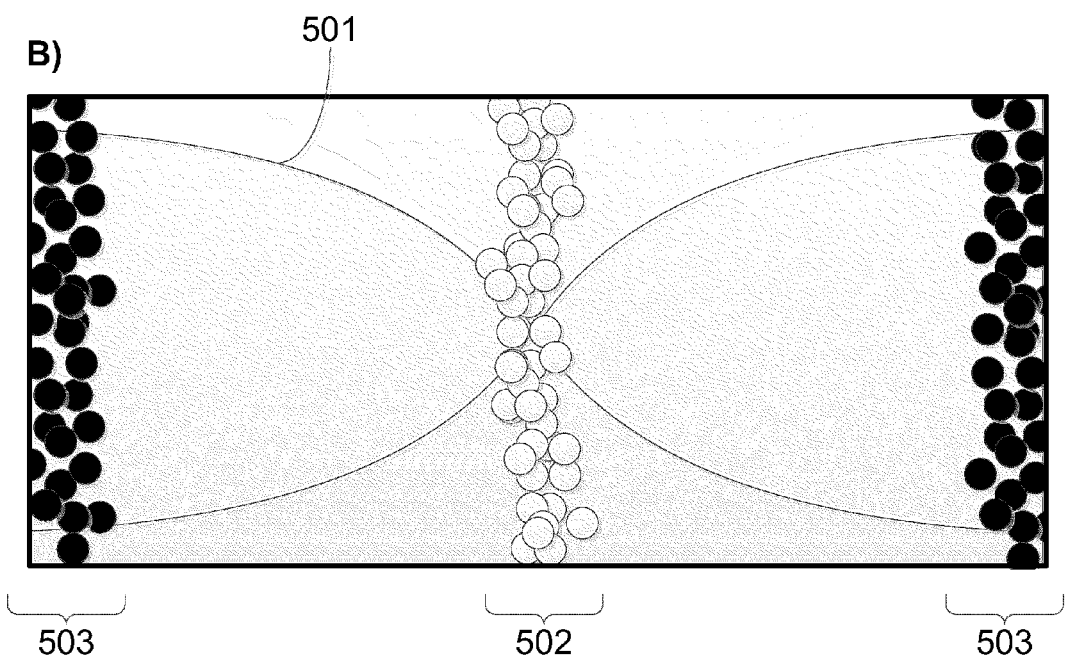

In some implementations, the dimensions of the separation channels are selected based on the wavelength of the imposed standing wave such a pressure node exists at about the center or other interior axis of the separating channel, while antinodes exists at about the walls of the separation channel. Particles are driven to different positions within the channel based on the sign of their acoustic contrast factor at a rate that is proportional to the magnitude of their contrast factor. Particles with a positive contrast factor (e.g., blood factors) are driven towards the pressure node within the interior of the separation channel. In contrast, particles with a negative contrast factor are driven toward the pressure antinodes. These principles are depicted and described further in relation to FIGS. 5A and 5B.

Based on these principles, blood factors can be separated from lipid-based capture particles with bound organophosphates, e.g., parathion and/or paraoxon, in two ways. In one way, as described further in relation to FIGS. 2 and 10, lipid-based capture particles with bound organophosphates are selected to have negative contrast factors, which is opposite to the positive contrast factors of the blood factors. Thus, in response to the standing acoustic wave, the blood factors are driven towards the resulting pressure node while the lipid-based capture particles with bound organophosphates are driven towards the antinodes.

This technique can be used in a single-stage separation system. As whole blood, organophosphates, e.g., parathion and/or paraoxon, and lipid-based capture particles mix in the mixing chamber 104 and continue to mix as flowing through the manifold system 107, the lipid-based capture particles bind to the parathion and/or paraoxon. As the whole blood, organophosphates, and lipid-based capture particles enter the area of the separation channel where the standing acoustic wave is imparted, the standing acoustic wave drives the lipid-based capture particles and bound organophosphates to a specific axis (e.g., against the wall of the separation channel) and the blood factors of the whole blood to a second axis (e.g., the middle of the separation channel). Thus, the lipid-based capture particles bound with organophosphates can be collected from the edges of the separation channel and disposed of while the cleaned blood is collected and returned to the patient.

Alternatively, lipid-based capture particles can be separated from formed blood factors based on a time of flight principle. That is, if the lipid-based capture particles are selected to have a contrast factor that is the same sign as that of the blood factors, but with a substantially different magnitude, and assuming the blood factors and lipid-based capture particles are substantially aligned prior to the application of a standing wave at a distance away from the positive pressure node induced by the wave, the blood factors and lipid-based capture particles will migrate towards the pressure node at different rates. Thus, the blood factors and lipid-based capture particles can be collected separately at a point where the higher contrast factor particles (lipid-based capture particles or blood factors depending on the selected lipid-based capture particles) have move sufficiently far from the initial aggregation axis that they have separated from the lipid-based capture particles due to their difference in acoustophoretic mobility. Thus, in some implementations, a two-stage separation process is employed. In the two-stage process, blood factors and lipid-based capture particles are first aggregated along a common first axis of the separation channel using a first standing acoustic wave. Then after they have reached the common aggregation axis, a second standing acoustic wave drives the blood factors and lipid-based capture particles to a second aggregation axis. However, instead of waiting until the blood factors and lipid-based capture particles all reach the second aggregation axis, the channel splits to direct the particles having the lower acoustophoretic mobility down a first outlet. The particles that have a greater acoustophoretic mobility, which would have already migrated towards the second aggregation axis to a point that they are beyond entrance to the first outlet, flow out a second outlet. This separation technique is described further in relation to FIGS. 3 and 10.

As illustrated in the system 100, the cleansed blood exits the microfluidic flow chamber 108 at a first outlet 110. From there the blood is returned to the patient 101 via an intravenous supply line 111. In some implementations, the blood in the supply line 111 is reheated to body temperature before returning to the patient 101. In other implementations an infusion pump is used to return the blood to the patient 101, while in the system 100 the pressure generated in the system by pumps 103 and 106 is adequate to force the blood to return to the patient 101.

As illustrated in the system 100, waste material (e.g., the lipid-based capture particle bound with parathion and/or paraoxon) exit the microfluidic flow chamber 108 and enter a waste collection unit 113. In some implementations, the waste collection unit 113 contains a lipid-based capture particle recycler. The lipid-based capture particle recycler unbinds the parathion and/or paraoxon from the lipid-based capture particles. The lipid-based capture particles are then returned to the reservoir 107 via tubing 114. The organophosphates, e.g., parathion and/or paraoxon, are then disposed of. In some implementations, the organophosphates are saved for further testing.

While the system 100 is described above for the in-line cleansing of a patient's blood, in alternative implementations, the system 100 can be used to cleanse stored blood. For example, the system 100 can be used to cleanse collected blood for later infusion to help ensure the safety of the blood.

Figure 2:
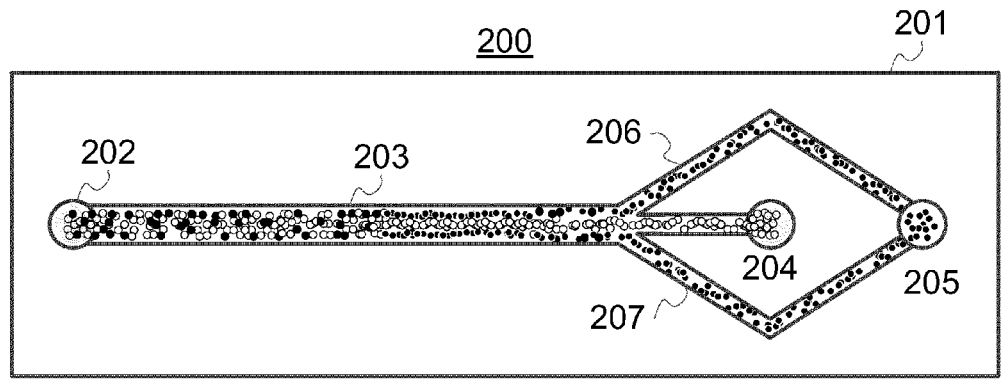
FIG. 2 is a non-limiting, exemplary top view of a single-stage separation channel, such as can be used in the system of FIG. 1.

FIG. 2 illustrates an example single-stage separation channel suitable for use within the microfluidic flow chamber 108 of the blood cleansing system 100. The separation channel includes an inlet 202, a flow channel 203, a first outlet 204, a first outlet channel 206, a second outlet channel 207, and a second outlet 205. The separation channel is manufactured in a sheet of material 201.

In FIG. 2, whole blood, parathion and/or paraoxon, and lipid-based capture particles enter the separation channel at the inlet 202 from the manifold system 107. The whole blood, organophosphates, e.g., parathion and/or paraoxon, and lipid-based capture particles then flow the length of the flow channel 203. The flow channel is subdivided into three regions: an upstream region, a downstream region, and a migration region. The migration region lies between the upstream and downstream regions, and is the region of the flow channel where the standing acoustic wave is imparted transverse to the flow of particles. As the blood factors of the whole blood, lipid-based capture particles and the organophosphates, enter the migration region, the standing acoustic wave drives the lipid-based capture particles bound to the organophosphates, e.g., parathion and/or paraoxon, to the side walls of the separation channel, and the blood factors of the whole blood to the center of the channel. The blood factors of the whole blood then exit the separation channel through the outlet 204 located at about the central axis of the separation channel. The lipid-based capture particles and organophosphates, then exit the separation channel through the first and second outlet channels 206 and 207, which terminates in the second outlet 205. In some implementations, the blood factors are driven to the walls of the separation channel and the lipid-based capture particles with bound organophosphates remain in the center of the separation channel.

In some implementations, the separation channel 200 can separate organophosphates, e.g., parathion and/or paraoxon, from any fluid. As discussed above and later in relation to FIGS. 5 and 7, the separation channel 200 can be used to remove parathion and/or paraoxon from any fluid. For example, the separation channel 200 may be used to remove organophosphates, e.g., parathion and/or paraoxon, from, but not limited to, blood plasma, blood serum, water, and lymph.

In the implementation of FIG. 2, the outlet 205 is formed from the merging of two outlet channels 206 and 207. In some implementations, the streams do not rejoin, but lead to separate outlet terminals.

In FIG. 2, the particles are separated in the same plane as the sheet of material 201 (i.e., particles are aligned to the left, right, or center of the channel); however, in other implementations, the particles are separated out of plane. For example, in some implementations, the particles are aligned with the top, middle, or bottom of the channel.

In FIG. 2, the sheet of material 201 can include, but is not limited to, polystyrene, glass, polyimide, acrylic, polysulfone, thermoplastic, and silicon. The channel can be manufactured by a number of manufacturing techniques, including, but not limited to, milling, embossing, and etching. In some embodiments, the channels are microchannels of polystyrene. In some embodiments, the channels are microchannels of thermoplastic.

In some implementations, the channels are made from 1 mm thick conventional polystyrene sheets, and seal using adhesiveless thermocompression bonding at 95° C. In some implementations, the channels are made from machining and bonding methods, see Tsao, C. and DeVoe, D., *Microfluidics and Nanofluidics*, 6(1): 1-16 (2009), that result in post-bond dimensional accuracy to within 10 μm and bonds that withstand up to 300 kPa internal pressure.

In some implementations, a higher frequency standing acoustic wave can be applied to create two pressure nodes within the separation channel 200, both spaced apart from the sidewalls of the channel and separated by an anti-node. In one such implementation, the blood factors in the blood aggregate into two substantially parallel streams near the sidewalls along the pressure nodes, while the lipid-based capture particles migrate to the center of the channel in line with the anti-node. In such implementations, the lipid-based capture particles exit the separation channel through the outlet 204, while the blood exits the separation channel through the first and second outlet channels 206 and 207.

Figure 3:
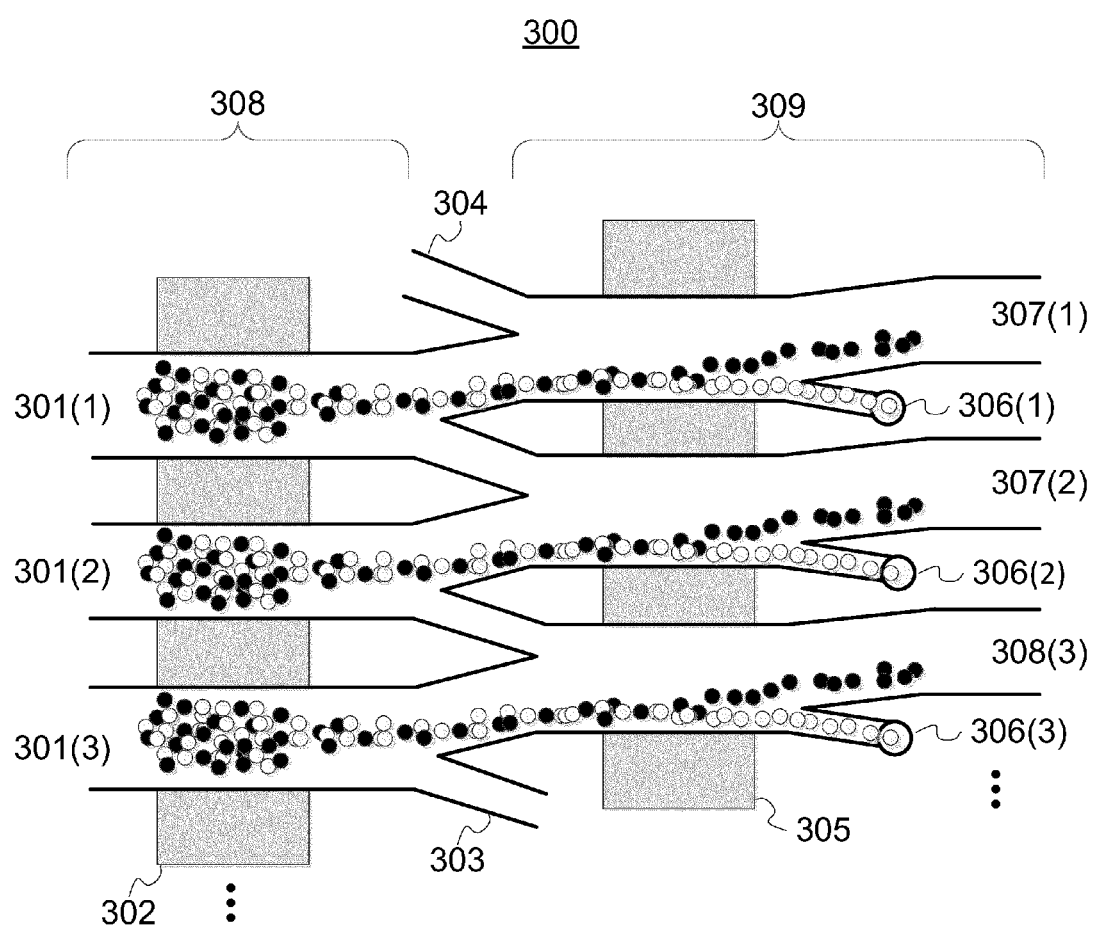
FIG. 3 is a non-limiting, exemplary top view of a network of two-stage separation channels, such as can be used in FIG. 1.

FIG. 3 illustrates an example network 300 of multistage separation channels suitable for use the blood cleansing system 100 depicted in FIG. 1. The network of separation channels includes a plurality of first inlets 301. FIG. 3 also includes first and second acoustic bulk transducers 302 and 305, respectively. Additionally, each separation channel includes an upstream outlet 303 and a second inlet 304. The upstream outlet 303 of each channel is connected to the second inlet 304 of its neighboring channel. The fluid exits the separation channels through a first downstream outlet 307 or second downstream outlet 306.

In each separation channel of the network 300, the flow channel through which most of the fluid in the channel flows shifts after the upstream outlet 303. The portion of the separation channel prior to the shift is referred to as the upstream portion 308 and the portion after the shift is referred to as the downstream portion 309. As the particles within the blood continue to flow down the separation channel, one subset of particles is driven into a first downstream outlet 307 and a second subset of the particles are driven into a second downstream outlet 306. For example, the cleaned blood exits through the first downstream outlet 307 and the lipid-based capture particles with bound organophosphates, e.g., parathion and/or paraoxon, exits through the second downstream outlet 306.

As described above, and illustrated in FIG. 3, the separation channels in the network 300 are generally divided into upstream portions 308 and downstream portions 309. The two portions are distinguished by a shift in the separation channel. The angle of the shift is referred to as the branching angle. The branching angle for a particular implementation is chosen to substantially align a wall of the downstream portion 309 with an interior axis of the upstream portion 308. The selected axis corresponds to the location of a pressure node induced in the channel by the first acoustic transducer 302. For example, in some implementations, a wall of the downstream portion 309 is configured to align with an interior axis substantially in the middle of the upstream portion 308.

In the illustration of FIG. 3, there is a plurality of first inlets 301. The number of first inlets, and thus separation channels, can be increased to n where n is the number of separation channels required to meet the flow demands of a specific implementation. In some implementations, the first inlets 301 are configured to accept flowing whole blood and a plurality of lipid-based capture particles. The flowing whole blood includes plasma, a plurality of blood factors and a plurality of OP molecules, such as, e.g., parathion and/or paraoxon. The blood factors of blood can include leukocytes (white blood cells), erythrocytes (red blood cells), and thrombocytes (platelets). In some implementations, the lipid-based capture particles begin binding to the OP (e.g., parathion and/or paraoxon) as they are mixed as they flow down the length of the upstream portion 308. In other implementations, the lipid-based capture particles are mixed with the whole blood prior to flowing through the first inlet 301, and thus the binding of the lipid-based capture particles and the OP (e.g., parathion and/or paraoxon) can begin before the blood is flowed through the first inlet 301.

As the fluid in the separation channels flows downstream it passes over a first bulk acoustic transducer 302 and eventually a second bulk acoustic transducer 305. The bulk acoustic transducers 302 and 305 impart standing acoustic waves on the separation channels. The standing acoustic waves are transverse to the flow of fluid through the separation channels. In some implementations, the acoustic bulk transducers 302 and 305 emit standing acoustic waves of different wavelengths. In other implementations the acoustic bulk transducers 302 and 305 emit standing acoustic waves of the same wavelength. Example acoustic waves can have, but are not limited to, wavelengths between about 1.0 and about 4.0 MHz, or between about 1.5 and about 3.5 MHz, or between about 2.0 and about 3.0 MHz.

In the network 300, the first acoustic bulk 302 transducer aligns the blood factors, lipid-based capture particles, and parathion and/or paraoxon in the interior of the upstream portions 308 of the separation channels. After the particles in the fluid are aligned in the middle of the flow channels, the channels angle to align the particles with walls of the downstream portions 309. With all particles aligned in the middle of the flow channel, fluid substantially away from the middle is free of lipid-based capture particles and OP, e.g., parathion and/or paraoxon, Thus, at the angle in the flow channels, a portion of the fluid, substantially void of blood factors, lipid-based capture particles and OP, exits through the upstream outlets 303. The particles continue to flow downstream, now substantially aligned with a wall of the respective downstream portions 309. Fluid entering the downstream portions 309 of the separation channels from the second inlets 304 ensures continued flow of the blood factors and lipid-based capture particles through the downstream portions of the 309 of the separation channels.

In the second stage particles are separated based on the speed at which (and thus distance) they travel from a given aggregation axis towards a second pressure node induced in the channel by a second standing acoustic wave. As indicated above, due to the angling of the separation channels, the blood factors and lipid-based capture particles enter the downstream portions of the separation channels aggregated along one wall.

As the particles flow along the wall of the separation flow channels, they pass over a second bulk transducer 305, which emits a second standing acoustic wave transverse to the flow of the particles. The second standing acoustic wave drives the particles away from the wall. Based on the magnitude of their contrast factor, a first subset of particles (e.g., the blood factors of blood) moves away from the wall at a faster rate than a second subset of particles (e.g., the lipid-based capture particles bound with parathion and/or paraoxon).

This differential rate of movement is achieved by using lipid-based capture particles that have an acoustophoretic mobility that is substantially different from that of the blood factors of blood. The different acoustophoretic mobility is in turn based on the magnitude of the contrast factor of lipid-based capture particles being substantially different from the magnitude of the contrast factor of the blood factors of blood. The speed at which the two groups move away from the wall can be calculated, and the rate of flow of blood through the system is known. Thus, the distance the blood factors will be moved away from the wall of a separation channel at a given location after being exposed to the second acoustic standing wave can also be calculated. This distance is termed d(f,x), where d is the distance traveled away from the wall given a specific fluid flow rate (f) and a specific distance (x) after the application of the standing acoustic wave. Based on this calculation, the separation channel can be divided into two outlets. The second downstream outlet 306 is positioned along the wall the blood factors and lipid-based capture particles were previously flowing. The second downstream outlet 306 is constructed to have a width just smaller than d(f, x). Thus, the blood factors, having traveled a distance of d(f,x) away from the wall due to the second standing acoustic wave would have been driven beyond the second outlet by the time they reach the distance (x), and thus are driven into the first downstream outlet 307. In contrast, the lipid-based capture particles bound to the parathion and/or paraoxon, having traveled a distance substantially less than d(f,x) due to their lesser acoustophoretic mobility, remain substantially near the wall of the downstream portion 309 and exit the second outlet 306. In some implementations, the distance (x) traveled between exposure to the standing acoustic wave and entering the first downstream outlet 307 is between about 1 and about 10 cm.

Figure 4:
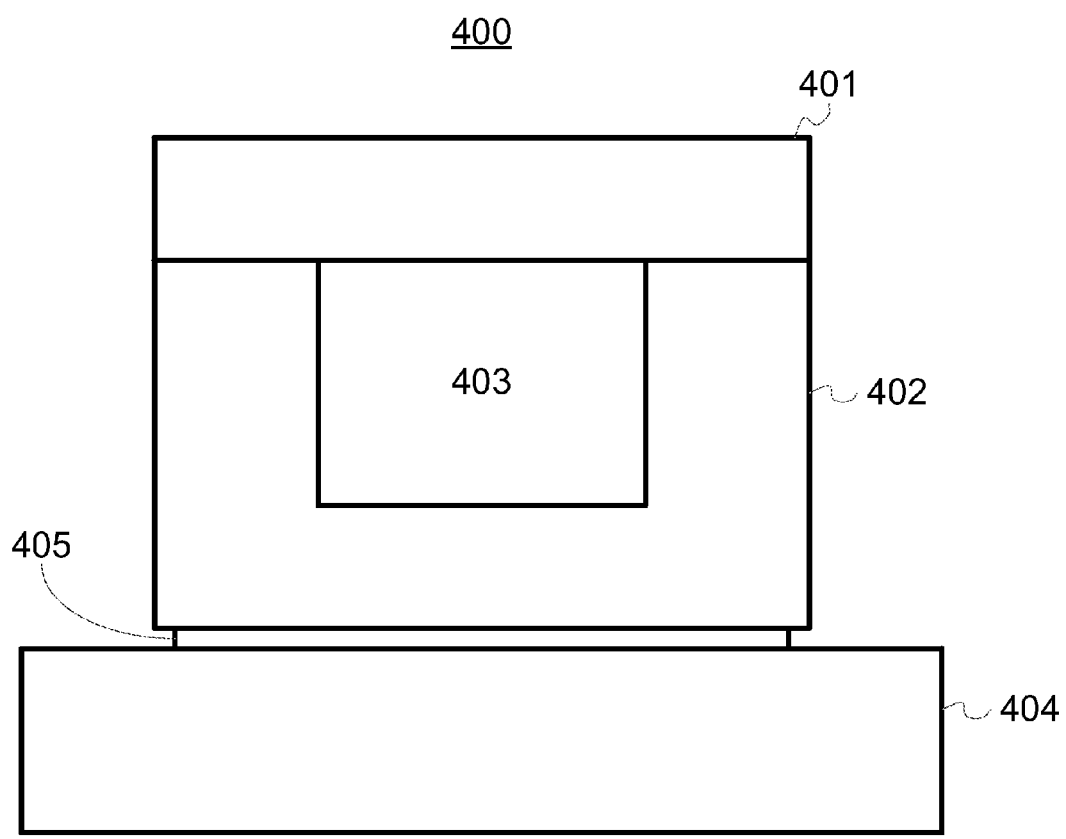
FIG. 4 is a non-limiting, exemplary cross sectional view of a single-stage separation channel, such as the separation channel of FIG. 2, mounted to a bulk transducer.

FIG. 4 is an illustrative cross-section of a separation channel 400 similar to the separation channel depicted in FIG. 2. The separation channel 400 includes a top layer 401 sitting atop a bottom layer 402. A channel is created in the bottom layer 402. When the top layer 401 is placed on the bottom layer 402 a lumen 403 is created. The separation channel 400 sits atop a bulk piezoelectric transducer 404. The separation channel 400 is secured to the bulk transducer 404, by a coupling adhesive 405 and/or mechanical clamp. In some implementations, the coupling adhesive is cyanoacrylate glue.

The bottom layer 402 and top layer 401 of the separation channel 400 are manufactured from a substrate sheet. The substrate sheet can be made of, without limitation, polystyrene, glass and polyimide, polyacrylic, polysulfone, thermoplastic, and silicon. In some implementations, the bottom layer 402 is manufactured by milling, embossing, and/or etching. After creating the two layers, they can be joined together by thermacompression, mechanical clamping, adhesive bonding, and/or plasma bonding. As described above, the separation channel sits atop an acoustic bulk transducer 404. The transducer 404 imparts a standing acoustic wave of a specific wavelength ($\lambda$) across the channel. The dimensions of the bottom layer 402, top layer 401, and lumen 403 are dependent on the selected wavelength. The width of the lumen 403 is equal to about half the wavelength ($\lambda_{fluid}/2$) of the acoustic wave in the fluid. The thickness of the side wall is equal to about a multiple of one quarter of the wavelength ($n \times \lambda_{wall}/4$) of the acoustic wave in the solid channel wall. The height of the lumen is preferably less than one quarter of the wavelength ($<\lambda_{fluid}/4$) of the acoustic wave in the fluid, and the thickness of the top layer 401 can be arbitrarily selected; however, in some implementations is chosen to be greater than one quarter of the wavelength ($>\lambda_{wall}/4$) of the acoustic wave in the solid channel wall.

In some other implementations, the bottom layer 402, top layer 401, and lumen 403 can have different relative dimensions. For separation channels 400 formed from a thermoplastic, such as polystyrene, polyimide, polyacrylic, or polysulfone, the width of the lumen 403 in the bottom layer 402 is less than the one-half the wavelength of the acoustic wave in the fluid. In some implementations, the width of the lumen 403 in a thermoplastic separation channel 400 is between about one-fourth and three-eighths the wavelength of the acoustic wave in the fluid (i.e., about 25%-50% narrower than the half the wavelength, as suggested above). The shorter width results from the smaller impedance mismatch between the thermoplastic walls of the separation channel and the fluid passed through the channel. This lower mismatch provides imperfect acoustic reflection, thereby motivating the narrower channel. Particularly in comparison to glass or silicon-based separation channels, thermoplastic separation channels are substantially less expensive to manufacture.

In one implementation, a separation channel formed from polystyrene can operate with an acoustic wave having a 1.0 and about 4.0 MHz, or between about 1.5 and about 3.5 MHz, or between about 2.0 and about 3.0 MHz. Assuming the channel is configured for carrying water, the lumen of the separation channel may be about 0.4 mm wide, or about 40% narrower than half the wavelength of the wave. Moreover, the sidewalls of the bottom layer 402 of a thermoplastic-based separation channel may be significantly wider than sidewalls formed from materials that serve as better acoustic reflectors.

In some implementations, the channel cross section is a shallow rectangle with its width, w, matched to one half the wavelength, λ, of sound in the fluid (i.e., the blood plasma). In some implementations, the wavelength depends on the chosen frequency, f, and is obtained from reference tables of acoustic velocity, c, according to the relation λ=c/f. In some implementations, the nominal channel width is set to w=c/(2f), in order to achieve a resonant standing half-wave across the fluid-filled channel. In some implementations, the acoustic focusing is between about 1.0 and about 4.0 MHz, or between about 1.5 and about 3.5 MHz, or between about 2.0 and about 3.0 MHz. In some implementations, the channel widths are in the range of about 0.2 to 0.8 mm.

FIGS. 5A and 5B are cross sectional views of particles suspended in a fluid as they flow through a separation channel similar to the separation channel 200. For FIGS. 5A and 5B, the flow of the fluid is transverse to the plane of the drawings. In some implementations, the fluid is whole blood, and the particles are the blood factors and lipid-based capture particles. For illustrative purposes, FIGS. 5A and 5B contains two particles, red blood cells (white dots) and lipid-based capture particles (black dots). FIG. 5A illustrates blood flowing through a channel without a standing acoustic wave being imparted on the channel and its contents. In FIG. 5A, the particles remain homogenously mixed throughout the channel. In FIG. 5B, a standing wave is imparted on the channel. The standing acoustic wave 501 creates two node types. A pressure node occurs at 502. The node extends across the full height of the lumen. The channel dimensions set forth above in relation to FIG. 4 yield a pressure node at approximately the center of the channel.

Particles are aligned based on the sign of their contrast factor. Particles with a positive contrast factor (e.g., the blood factors of blood) are driven towards a pressure node 502. In contrast, particles with a negative contrast factor (e.g., lipid-based capture particles used in the single-stage device described above) are driven toward the pressure antinodes 503.

Figure 6:
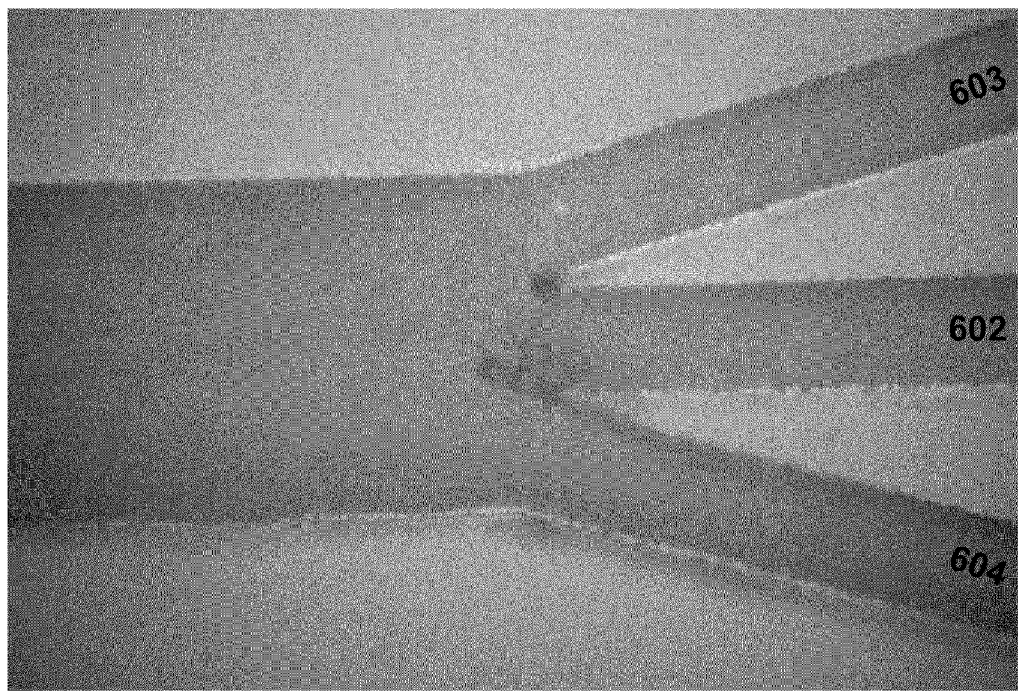
FIG. 6A is a non-limiting, exemplary top view of a separation channel, as depicted in FIG. 2, in which fluid flows through the channel without the application of the standing acoustic wave.
FIG. 6B is a non-limiting, exemplary top view of a separation channel, as depicted in FIG. 2, after the application of a standing acoustic wave.
Figure 6:
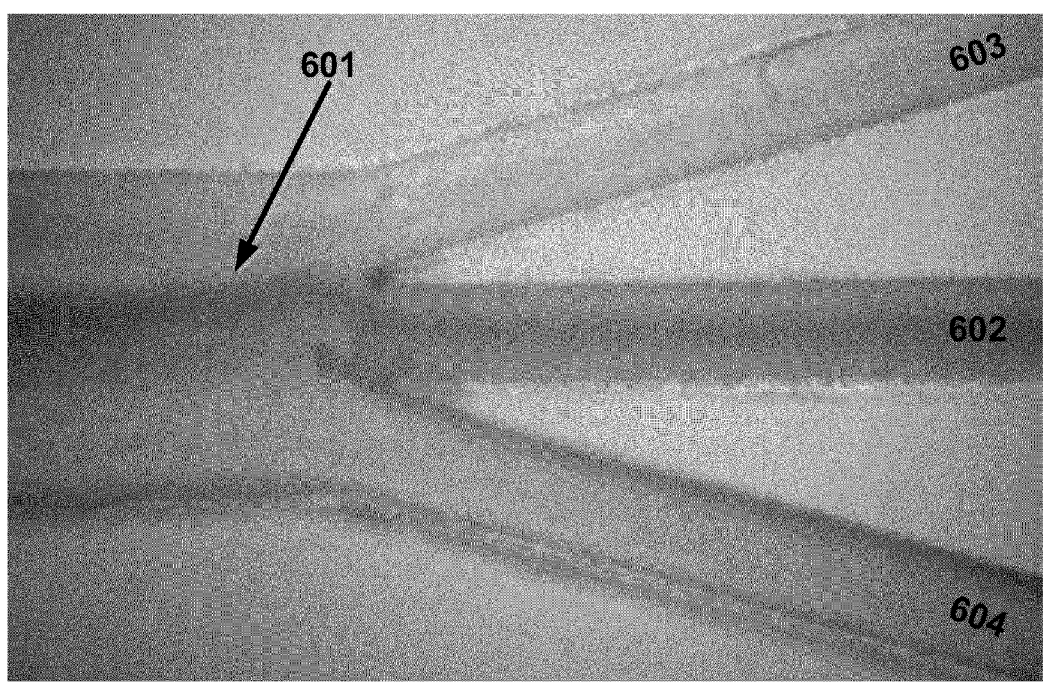

FIG. 6A is a top view of a separation channel 600, as depicted in FIG. 2, in which fluid is flown through the separation channel 600 without the application of the standing acoustic wave. The separation channel 600 includes three outlets 602, 603 and 604. As with FIG. 5A, particles suspended in the fluid are homogeneously distributed throughout the fluid, and thus are not readily discernible in the image. The particles flow substantially evenly out of all three outlets 602, 603 and 604.

In contrast, FIG. 6B is a top view of the separation channel 600, as depicted in FIG. 2, after the application of a standing acoustic wave, according to one illustrative embodiment.

In FIG. 6B, as a result of the standing acoustic wave, the particles 601 suspended in the fluid is aligned with the middle of the separation channel 600. Once aligned with the middle of the separation channel 600, the particles 601 exit the separation channel 600 through the middle outlet 602. The remaining fluid, substantially devoid of particles, exits the separation channel through the side outlets 603 and 604.

Figure 7:
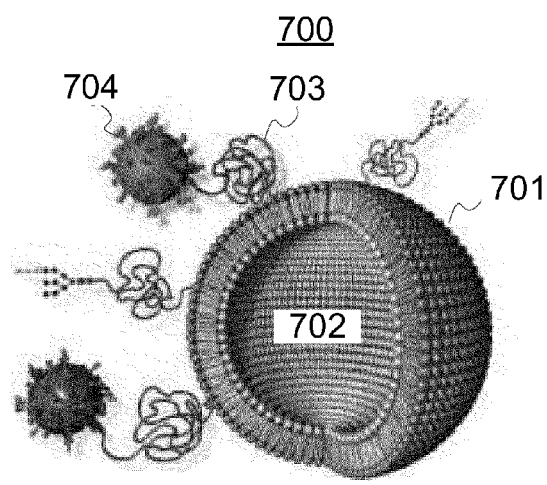
FIG. 7 is a non-limiting, exemplary cut away of a lipid-based capture particle.

FIG. 7 is an illustrative example of a lipid-based capture particle 700 in the form of a liposome. The lipid-based capture particle 700 includes a lipid bilayer 701 encapsulating a fluid 702. Displayed on the surface of the lipid bilayer are BChE molecules 703. The BChE molecules bind and liposome capture parathion and/or paraoxon 704 and or other OP toxins.

More specifically, the lipid bilayer 701 forms a lipid-based capture particle. In some implementations, the lipids may be, but are not limited to 1,2-dioleoyl-sn-glycero-3-phosphocholine (DOPC), 1,2-dioleoyl-sn-glycero-3-phospho-(1'-rac-glycerol) (DOPG), 1,2-dioleoyl-sn-glycero-3-phosphoethanolamine (DOPE), or a combination thereof. The lipid-based capture particle is tuned for acoustically induced mobility. Entities that differ in size, density, and/or compressibility have the greatest differential mobility in acoustic fields and thus are the most readily separable. Therefore, in some implementations, the size, density, and/or compressibility of the lipid-based capture particles is modified to distinguish the lipid-based capture particle from the blood factors of blood. In some implementations, the acoustic mobility of a particle is proportional to its volume. For example, in some implementations, the lipid-based capture particles are between about 2 μm to 35 μm, or between about 5 μm to 30 μm, or between about 10 μm to 25 μm, or between about 15 μm to 20 μm in diameter. In some implementations, use of such larger lipid-based capture particles results in a more distinct separation between the lipid-based capture particles and red blood cells.

In implementations that adjust the compressibility of the lipid-based capture particle, the rigidity of the lipid-based capture particle can be adjusted by controlling the lipid components in lipid-based capture particle. The length and saturation of the lipid hydrocarbon tail, cross-linking of the hydrophobic domains, and/or the inclusion of cholesterol, and/or PEG will all affect the fluidity and compressibility of a lipid-based capture particle.

In other implementations, the density of the lipid-based capture particle, e.g., in the form of a liposome, is engineered by encapsulating an acoustically active fluid 702. In these implementations the acoustical active molecule can be an ultra sound imaging contrast agent, glycerine, castor oil, coconut oil, paraffin, air, and/or silicone oil.

In other implementations, all of the above described characteristics are manipulated to create a lipid-based capture particle with the greatest possible difference in contrast factor compared to a formed element.

As described above, the acoustically induced mobility of a particle is based on the contrast factor of the particle. For a lipid based lipid-based capture particle, the contrast factor is dominated by the properties of the encapsulated fluid. The contrast factor is based on the bulk modulus (K) and density ($\varrho$) of the encapsulated fluid. When suspended in blood, the contrast factor (?) for a lipid-based capture particle, encapsulating a specific fluid, is calculated with the below equation:

$$\varphi = \frac{5\rho - 2 \cdot 1.02}{2\rho + 1.02} + \frac{2.2}{K}$$

Table 1 provides the $e\tau$, K, and then calculated ?-factor based on the above equation.

TABLE 1

Calculated Contrast Factors

| | Materials | $e\tau$ (g/ml) | K(Gpa) | ? |
|---|---|---|---|---|
| Encapsulated Fluids | glycerine | 1.25 | 4.7 | +0.73 |
| | castor oil | 1.03 | 2.06 | −0.06 |
| | coconut oil | 0.92 | 1.75 | −0.36 |
| | paraffin | 0.80 | 1.66 | −0.58 |
| | silicone oil | 1.04 | 1.09 | −1.00 |
| | air | 0.002 | 1.4 | −3.55 |
| Blood factors | white blood cell | 1.02 | 2.5 | +0.12 |
| | red blood cell | 1.10 | 3.0 | +0.34 |

In some implementations, such as the implementation of FIG. 3, the lipid-based capture particles have a contrast factor that is lower in magnitude, but still of the same sign as the blood factors. In these implementations, the low contrast factor of the lipid-based capture particles can be achieved by making the lipid-based capture particles sufficiently small to reduce their contrast factor to below that of the blood factors.

Figure 8:
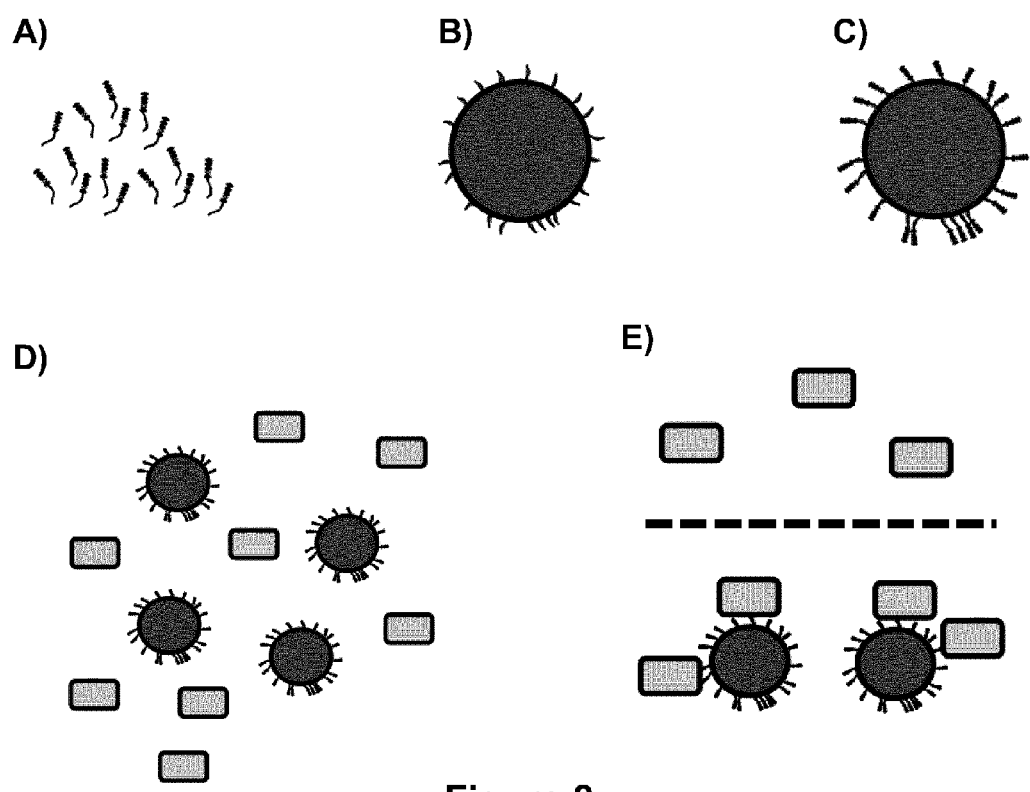
FIGS. 8A-E are non-limiting, exemplary illustrations of the components included in a lipid-based capture particle, as depicted in FIG. 7.

FIG. 8 illustrates an overview of the process of making and using a lipid-based capture particle. The OP affinity molecules (e.g., BChE molecules for purposes of this illustrative implementation) of FIG. 8A are embedded in the lipid-based capture particle, (e.g., a liposome for purposes of this illustrative implementation) of FIG. 8B to produce BChE lipid-based capture particles as illustrated in FIG. 8C. Next, the lipid-based capture particles are combined with a blood or other fluid containing OP, e.g., parathion and/or paraoxon as illustrated in FIG. 8D. The parathion and/or paraoxon then bind to the lipid-based capture particles. FIG. 8E illustrates bound parathion and/or paraoxon can then be removed from the fluid by acoustically moving the lipid-based capture particles whereas parathion and/or paraoxon are not removed from the fluid.

Figure 9:
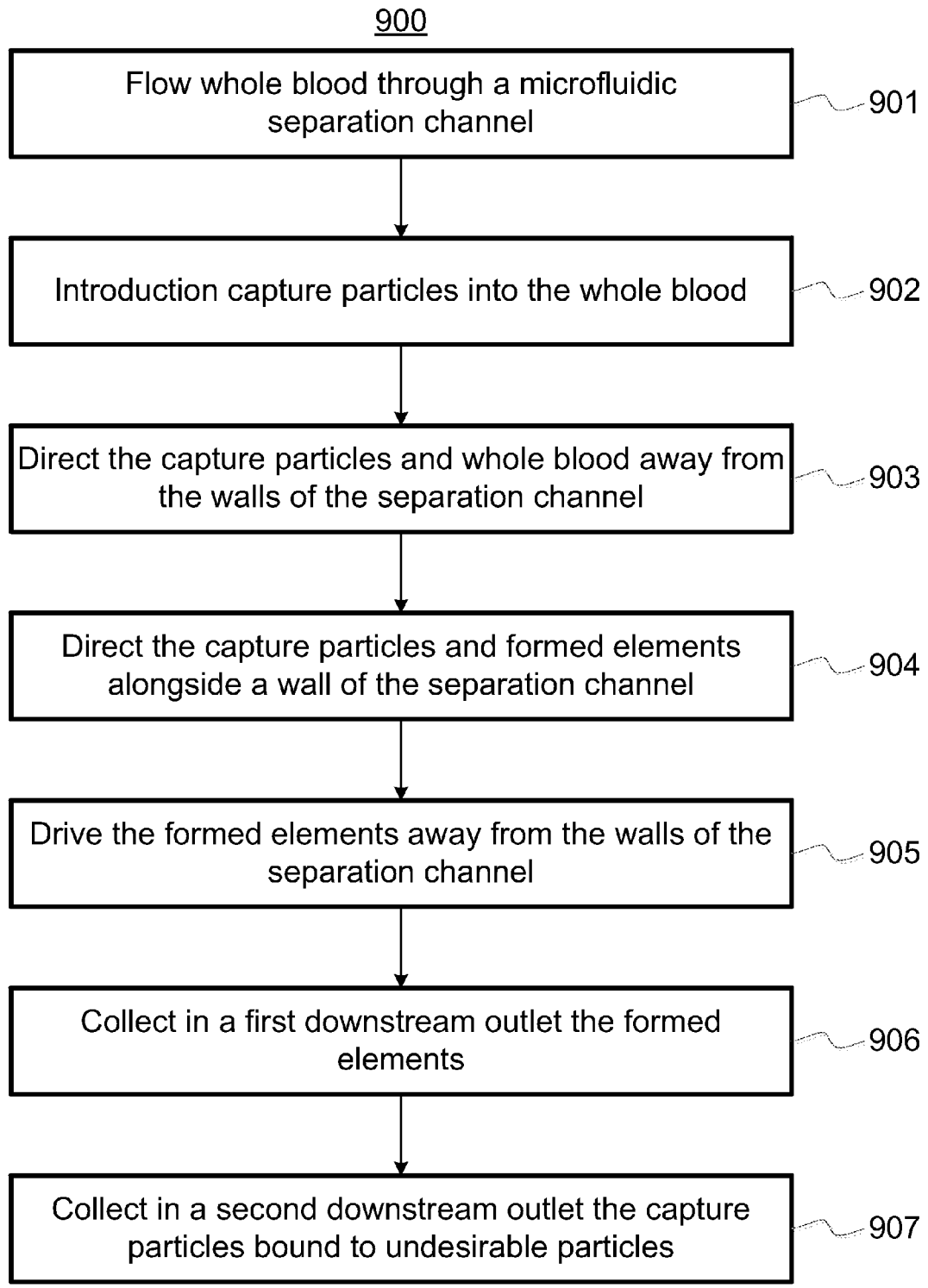
FIG. 9 is a non-limiting, exemplary flow chart of a method for cleansing blood with a two-stage separation channel, as depicted in FIG. 3.

FIG. 9 is a flow chart of a method 900 to cleanse blood of OPs such as parathion and/or paraoxon in a blood cleaning separation channel similar to the two-stage device described in FIG. 3. First whole blood is flowed through a microfluidic separation channel (step 901). Lipid-based capture particles are introduced into the whole blood (step 902). Then, blood factors of the blood and the lipid-based capture particles are directed away from the walls of the separation channel (step 903). Next, the lipid-based capture particles and blood factors are directed alongside a wall of the separation channel (step 904). Then, blood factors are driven away from the walls of the separation channel (step 905). Finally, the blood factors are collected in a first downstream outlet and the lipid-based capture particles are collected in a second downstream outlet (steps 906 and 907, respectively).

Referring to FIGS. 3 and 9, the method of cleansing blood includes flowing whole blood through a microfluidic separation channel (step 901). The whole blood contains plasma; a plurality of blood factors such as red blood cells, white blood cells, and platelets; and OP molecules, such as, e.g., parathion and/or paraoxon. In some implementations, the whole blood is flowed through a plurality of microfluidic separation channels, such as the network of channels 300, connected to one another by a manifold system, while in other implementations a single separation channel is used. In some implementations, the whole blood is extracted from a patient. In other implementations the whole blood is collected from a patient or donor and stored prior to cleansing.

Lipid-based capture particles are introduced into the whole blood (step 902). In some implementations, the lipid-based capture particles are introduced into the whole blood at the first inlet 301 of the separation channel depicted in FIG. 3. In other implementations, the lipid-based capture particles are introduced into the device's manifold system or in a mixing chamber upstream from the manifold. After introduction into the whole blood, the lipid-based capture particles begin to bind to the parathion and/or paraoxon in the whole blood.

Next, the method 900 continues with the lipid-based capture particles and the blood factors of the whole blood, which are, originally, substantially-evenly dispersed throughout the whole blood, being directed away from the walls of the separation channel (step 903) and aggregated into alignment at about the center of the separation channel. In some implementations, such as the implementation in the network 300 as described above, this is done with a first bulk transducer 302 imparting a standing acoustic wave across the channel transverse to the direction of flow within the channel in an upstream portion 308, resulting in a pressure node at about the center of the separation channel. In such implementations the contrast factor of the lipid-based capture particles has the same sign as that of the blood factors, thus the blood factors and lipid-based capture particles move in tandem towards the pressure node. This initial aggregation of particles along a common axis enables later separation of the lipid-based capture particles from the blood factors of blood due based on their differential acoustophoretic mobility.

As discussed above in reference to network 300, after an initial aggregation (step 903), the method 900 continues with the lipid-based capture particles and blood factors of blood being directed alongside a downstream wall of the separation channel (step 904). In some implementations, such as that of network 300, this is accomplished by a shift in the separation channel such that the downstream portion of the separation channel is significantly aligned with the middle of the upstream portion of the separation channel.

As depicted in FIG. 3 above, in the downstream portion 309, the method 900 continues with the blood factors being driven way from the walls of the separation channel (step 905). As mentioned above, in some implementations, the contrast factor of the blood factors and the lipid-based capture particles have the same sign but are of different magnitudes. Thus, the blood factors will migrate away from the wall at a faster rate than the lipid-based capture particles and organophosphates, e.g., parathion and/or paraoxon. In other implementations, the lipid-based capture particles are designed to have a contrast factor magnitude larger than the blood factors of blood, thus the lipid-based capture particles move away from the wall at a faster rate than the blood factors.

In some implementations, the standing waves applied to the upstream portion 308 and/or to the downstream portion 309 are periodically halted for a limited amount of time. Doing so allows lipid-based capture particles or blood factors that may have become trapped against a sidewall of the separation channel 300 to be released, thereby preventing clogging or congestion in the channel. For example, for devices utilizing an excitation frequency between about 1.0-3.04, the standing waves may be halted about once every second for about one tenth of second. In other implementations, the standing waves may be halted more or less frequently with shorter or longer durations depending, for example, on the length and width of the channel and the flow rate of fluid through the channel. In some implementations, the standing wave has a duty cycle of between about 75% and about 98%, or between about 78% and about 95%, between about 81% and about 92%, between about 84% and about 89%.

The method 900 concludes when the blood factors are collected in a first downstream outlet (step 906) and the lipid-based capture particles being collected in a second downstream outlet (step 907). As described above in relation to network 300, the second downstream outlet 306 is configured to collect fluid containing lipid-based capture particles substantially devoid of blood factors. In some implementations, this is achieved by configuring the width of the second downstream outlet 306 to be slightly less than d(f,x), the distance the blood factors travel in response to the standing acoustic wave given a flow rate off and a distance x from the point of application of the standing acoustic wave. Thus the blood factors, having been driven d(f,x) away from the separating channel will be collected in the first downstream outlet 307.

Figure 10:
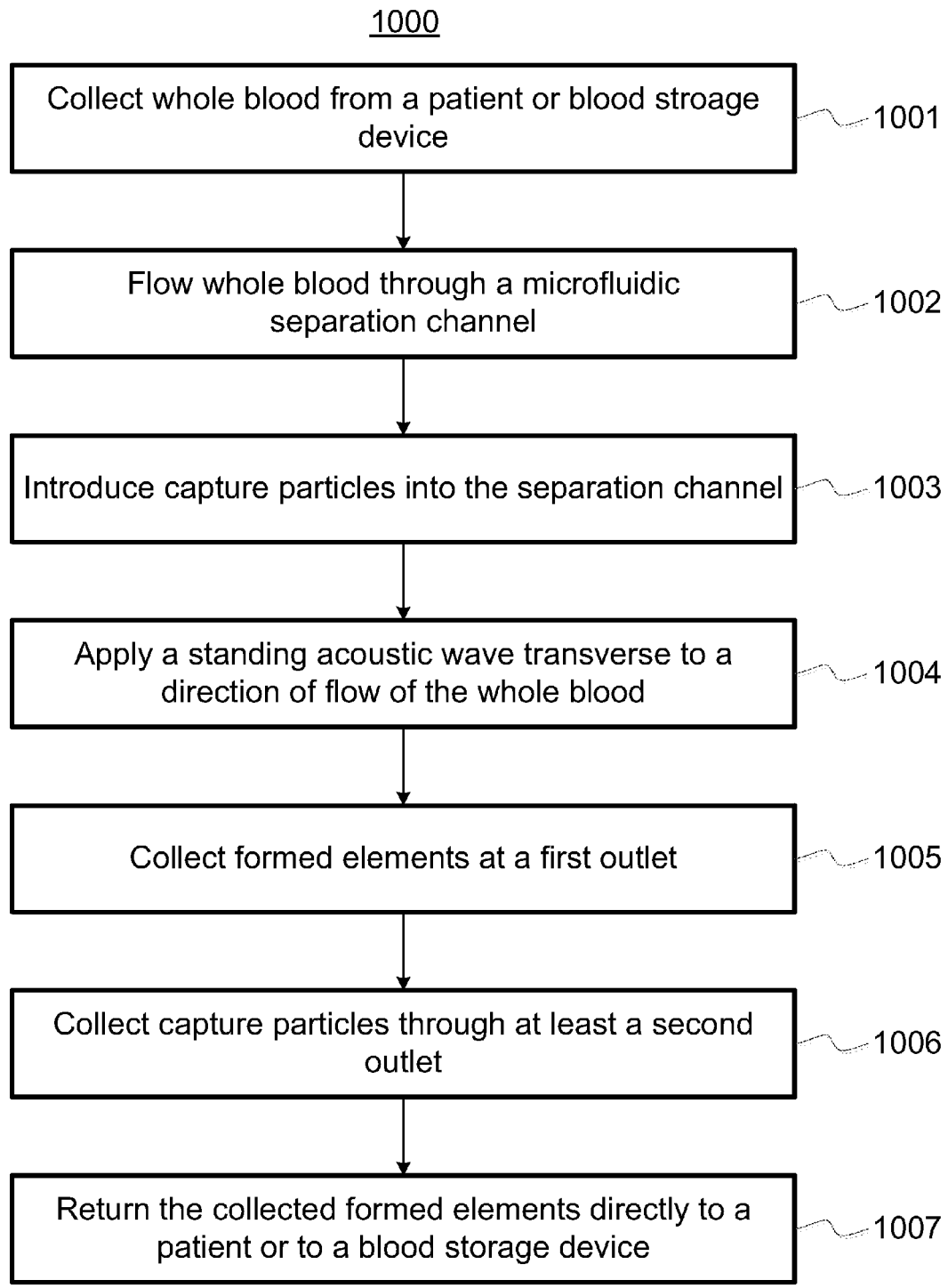
FIG. 10 is a non-limiting, exemplary flow chart of a method for cleansing blood with a single-stage separation channel, as depicted in FIG. 2.

FIG. 10 is a flow chart of a method for cleansing blood with a single-stage microfluidic separation channel (1000). First, whole blood is collected (step 1001). Then whole blood is flowed into an inlet of a single-stage microfluidic separation channel, as depicted in FIG. 2 (step 1002). Next, a plurality of lipid-based capture particles is introduced into the whole blood (step 1003). Then a standing acoustic wave is applied to the separation channel (step 1004). The blood factors are then collected in a first outlet (step 1005). Next, the lipid-based capture particles are collected in a second outlet (step 1006). Finally, the cleansed blood is returned to a storage container or returned directly to the patient (step 1007).

Referring to FIGS. 1, 2 and 10, the method 1000 of cleansing blood with a single-stage microfluidic separation channel 200 begins by collecting whole blood. In some implementations, the whole blood is collected from a patient 101, and then directly introduced into the blood cleansing system 100. In other implementations, the whole blood is collected from a patient 101 and then stored for later cleansing.

Next, the method 1000 of cleansing blood with a single-stage microfluidic separation channel 200 continues by flowing whole blood into the inlet of a microfluidic separation channel (step 1002). The whole blood contains a blood factors, plasma, and OP, e.g., parathion and/or paraoxon. In some implementations, a single microfluidic separation channel is used, while in others a plurality of single-stage separation channels is used in conjunction to accommodate greater blood flow throughput.

The method 1000 continues with the introduction of a plurality of lipid-based capture particles into the whole blood (step 1003). In some implementations, the constituent components of lipid-based capture particles are injected into a separation channel with a micronozzle and spontaneously form lipid-based capture particles as injected into the separation channel. In other implementations, the lipid-based capture particles are prefabricated and then introduced into the whole blood. In some implementations, the lipid-based capture particles are introduced into the whole blood after the whole blood enters the separation channel through the first inlet 202. In yet other implementations, the lipid-based capture particles are introduced into the whole blood before the blood enters through the first inlet 202 of the separation channel 200. In some implementations, the lipid-based capture particles are microbeads and/or lipid based liposomes.

Next, the method 1000 continues with the applying of a standing acoustic wave to the separation channel (step 1004). The standing acoustic wave is applied transverse to a direction of flow of the whole blood through the separation channel 200. In some implementations, the blood factors and lipid-based capture particles have contrast factors with different signs. Thus, the application of the standing acoustic wave causes the blood factors to aggregate about the central axis of the separation channel and the lipid-based capture particles to aggregate along at least one wall of the separation channel, as depicted in FIG. 2. In other implementations the standing acoustic wave causes the blood factors to aggregate along at least one wall of the separation channel and the lipid-based capture particles to aggregate about the central axis of the separation channel.

In some implementations, the standing wave is periodically halted for a limited amount of time. Doing so allows lipid-based capture particles or blood factors that may have become trapped against a sidewall of the separation channel 200 to be released, thereby preventing clogging or congestion in the channel. For example, for devices utilizing an excitation frequency between about 1.0-4.0 MHz, the standing wave may be halted about once every second for about one tenth of second. In other implementations, the standing wave may be halted more or less frequently or for shorter or longer durations depending, for example, on the length and width of the channel and the flow rate of fluid through the channel. In some implementations, the standing wave has a duty cycle of between about 75% and about 98%, or between about 78% and about 95%, between about 81% and about 92%, between about 84% and about 89%.

Then, the method 1000 continues with the collecting of the blood factors of the whole blood in a first outlet (step 1005). In some implementations, as depicted in FIG. 2, a first outlet 204 is aligned with the central axis of the separation channel allowing the outlet to collect the blood factors as they aggregate and flow down the central axis of the separation channel. Similarly, the method continues with the collecting of the lipid-based capture particles in a second outlet (step 1006). In some implementations, the end of the separation channel has at least a second outlet channel 206 and 207 aligned with at least one wall of the separation channel. As the lipid-based capture particles are driven towards the anti-pressure nodes along the walls of the separation channel, they are collected by the outlets channels 206 and 207 aligned with the walls of the separation channels. In some implementations, the standing acoustic wave is adjusted such that the formed particle align along the walls of the separation channel and the lipid-based capture particles align with the central axis of the separation channel. In such an implementation, the blood factors are funneled into outlets along the wall of the separation channel and the lipid-based capture particles are funneled into an outlet aligned with the central axis of the separation channel. In some implementations, the outlet channels 206 and 207 terminate in individual outlets or merge to terminate into a single outlet 205.

The method 1000 concludes with the reintroduction of the cleansed blood into a patient 101 or storage (step 1007). In some implementations, such as system 100, the whole blood is collected directly from a patient and then reintroduced to the patient 101. In some implementations, the cleansed blood is reheated to body temperature before being reintroduced into the patient 101. In other implementations, the cleansed blood is collected in a storage container for later reintroduction into a patient 101.

EXAMPLES

The present examples are non-limiting implementations of the use of the present technology.

Example 1

Preparation of Lipid-Based Capture Particles

Provided below is a non-limiting exemplary method for making a lipid-based capture particle in the form of a liposome.

Materials

Pyrromethene dye (Exciton #597-8C9), 1000 cSt Silicone oil (Sigma Aldrich #378399), 1,2-dilauroyl-sn-Glycero-3-[phosphor-rac-(1-glycerol)](Sodium Salt) (Avanti #840435P)/(Matreya, #1443), 1,2-dilauroyl-sn-glycero-3phosphocholine (Avanti #850702P) 18G syringe Liposofast-Basic (Avestin), PBS, 10 μm track etched membrane (Whatman #7060-4715), BChE (Protexia™), and PEG.

Method for Linking BChE to a Lipid Via PEG Linkers

BChE is linked to PEG-lipids, by dissolution of an activated functionalized lipid (such as DSPE-PEG-NH$_2$) in an organic solvent such as 1:2 ratio of DMSO/methanol followed by addition of BChE and coupling reagent EDC. The extent of the reaction is monitored by thin layer chromatography (TLC) using KMnO4 or p-anisaldehyde. The un-reacted lipid-PEG is extracted by gel electrophoresis.

Method for Making a Lipid-Based Particle Displaying BChE in the Form of a Liposome Emulsions are prepared through a multistep emulsification process by combining fluorescent DLPG-silicone oil with PBS. The oil mixture is prepared by dissolving positively charged DLPG (Matreya, 1443) and pyrromethene dye (Exciton, 597-8C9) into 1000 cSt silicone oil (Sigma Aldrich, 378399) for a final concentration of 0.5 mg/mL and 0.25 mg/mL, respectively. BChE-PEG-lipid is added to the oil mixture. Lipids and dye is allowed to equilibrate in the oil for at least 24 hours. Using an 18G syringe, the oil is then aspirated up and down through an equal volume of PBS, resulting in an aqueous phase and an oil phase. The aqueous phase is extracted with a larger 16G needle and loaded into one syringe of the liposofast (Avestin). A 10 μm track etched membrane (Whatman, 7060-4715) is inserted between the mesh bearings of the liposofast and locked into place. The emulsions are then extruded through the membrane by pushing the syringes of the liposofast back and forth 10 times. Lipid-based particles are analyzed with MatLAB.

In some implementations, the lipid-based particles produced above are dialyzed to remove small liposomes. Large pore dialysis is performed to remove liposomes less than 3 μm from the extruded liposomes. Dialysis cassettes (Thermo Scientific, 66810) are modified by replacing the original membrane with a 3 μm filtration membrane (Whatman, 111712). Membranes are attached with Dow Corning 3140 and allowed to cure at 65° C. for at least 12 hours. Freshly extruded liposomes are then added to the cassette and submerged into a beaker of PBS at a 1:100 ratio of liposome solution to PBS. The beaker was placed on a magnetic stirrer with stir-bar for 24 hours. After 24 hours, the solution containing liposomes greater than 3 μm was removed.

Example 2

Method for Clearing Parathion and/or Paraoxon from Guinea Pig Whole Blood

Samples of guinea pig blood are saturated with excess paraoxon. Lipid-based capture particles are added to the contaminated blood, blood without lipid-based capture particle treatment, and blood without paraoxon, are used as controls. The contaminated blood and controls are incubated at 37° C. for one hour. The contaminated blood and control are separately passed through a microfluidic device as described above. Samples are collected from the blood outlet stream and are processed and analyzed for free paraoxon concentration. The blood samples are analyzed for BChE activity according to the Ellman assay and compared to untreated control. These data are used to determine OP clearance efficiency and capacity of the filtration unit.

It is anticipated that the collected blood from the lipid-based capture particle treated sample will have less free paraoxon than the untreated blood sample, and will be comparable in purity to the control (no paraoxon). The results will indicated that the lipid-based capture particles of the present technology are useful for removing parathion and/or paraoxon from parathion contaminated blood.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

What is claimed is:

1. A device for removing organophosphates from whole blood comprising:
   a microfluidic separation channel having an upstream end and downstream end, the separation channel comprising:
      a first inlet configured to introduce flowing whole blood into a proximal end of the separation channel, wherein the whole blood includes or is suspected to include organophosphates;
      a first outlet at the downstream end of the separation channel positioned substantially along the longitudinal axis of the separation channel;
      a second outlet at the downstream end positioned adjacent a first wall of the separation channel; and
   an acoustic transducer positioned adjacent to the separation channel for imposing a standing acoustic wave transverse to the flow of blood through a particle migration region of the separation channel; and a lipid-based capture particle injector containing lipid-based capture particles and configured to introduce lipid-based capture particles into the whole blood before the blood reaches the particle migration region of the separation channel, wherein the lipid-based capture particle comprises a first population of lipids and silicon oil; wherein the first population of lipids comprises organophosphate affinity molecules linked to the lipids in the first population of lipids, wherein the organophosphate affinity molecule is BChE.

2. The device of claim 1, wherein the lipid-based capture particle further comprises a second population of lipids, wherein the second population of lipids form a lipid layer in which the first population is embedded.

3. The device of claim 1, wherein the lipid-based capture particles are in the form of a liposome, vesicle, emulsion, lipid encapsulated droplet, or combinations thereof.

4. The device of claim 1, wherein the organophosphate affinity molecules are linked to the first population of lipids with a PEG molecule.

5. The device of claim 1, wherein the silicone oil is encapsulated within the lipid-based particle.

6. The device of claim 1, further comprising a reservoir in fluidic communication with the lipid-based capture particle injector.

7. The device of claim 1, wherein the lipid-based particle is a liposome.

8. The device of claim 1, wherein the separation channel comprises walls having a thickness at a particle aggregation point that is greater than a multiple of one quarter of the wavelength of an acoustic wave acting on the walls of the separation channel.

9. A method of cleansing blood of a subject comprising:
flowing whole blood into an inlet of a microfluidic separation channel wherein the whole blood comprises plasma and blood factors, and includes or is suspected to include organophosphates;
introducing lipid-based capture particles into the whole blood which bind to the organophosphates, wherein the lipid-based capture particle comprises a first population of lipids and silicon oil; wherein the first population of lipids comprises an organophosphate affinity molecule linked to the lipids of the first population of lipids, wherein said organophosphate affinity molecule is BChE; and
applying a standing acoustic wave transverse to a direction of flow of the whole blood through the separation channel such that the blood factors aggregate to about the axial center of the separation channel and the lipid-based capture particles with bound organophosphates aggregate along at least one wall of the separation channel.

10. The method of claim 9, further comprising cycling off the standing acoustic wave such that the duty cycle of the standing acoustic wave is between about 75% and about 95%.

11. The method of claim 9, further comprising collecting blood factors of the whole blood at a first outlet positioned at a downstream end of the separation channel at about the axial center of the separation channel.

12. The method of claim 9, further comprising collecting lipid-based capture particles through at least a second outlet positioned at the downstream end of the separation channel adjacent to the at least one wall along which the lipid-based capture particles are aggregated.

13. The method of claim 9, wherein the lipid-based capture particles further comprises a second population of lipids, wherein the second population of lipids form a lipid layer in which the first population is embedded.

14. The method of claim 9, wherein the lipid-based capture particles have an opposite contrast factor than that of the blood factors.

15. The method of claim 9, wherein the lipid-based capture particles are between about 10 µm and 20 µm in diameter.

16. The method of claim 9, further comprising:
reintroducing the blood factors back into the subject after flowing the whole blood through the microfluidic separation channel.

17. A composition comprising organophosphate affinity molecules, a first population of lipids and silicon oil, wherein the organophosphates affinity molecules are linked to the first population of lipids, wherein the first population of lipids form a lipid-based capture particle, wherein the silicone oil is encapsulated within the lipid-based capture particle, and the organophosphate affinity molecules are displayed on the surface of the lipid-based capture particle, wherein said organophosphate affinity molecule is BChE.

18. The composition of claim 16, further comprising a second population of lipids, wherein the second population of lipids form a lipid layer in which the first population is embedded.

19. The composition of claim 16, wherein the first population of lipids is selected from DSPE, DPPE, DMPE, or a combination thereof.

20. The composition of claim 17, wherein the second population of lipids is selected from DOPC, DOPG, DOPE, or a combination thereof.

* * * * *